US012734271B2

(12) United States Patent
Floros et al.

(10) Patent No.: US 12,734,271 B2
(45) **Date of Patent: *Sep. 15, 2026**

(54) ADHESIVE DEVICES AND USES THEREOF

(71) Applicant: Cohesys Inc., Toronto (CA)

(72) Inventors: Michael C. Floros, Toronto (CA); Latchmi Raghunanan, Toronto (CA); Alexander J. Lausch, Toronto (CA); Janaina Freitas Bortolatto, Toronto (CA); Bryan Donovan Quan, Toronto (CA); Avinaash Antonio Persaud, Toronto (CA)

(73) Assignee: Cohesys Inc., Toronto (CA)

(*) Notice: Subject to any disclaimer, the term of this patent is extended or adjusted under 35 U.S.C. 154(b) by 826 days.

This patent is subject to a terminal disclaimer.

(21) Appl. No.: 17/825,751

(22) Filed: May 26, 2022

(65) Prior Publication Data

US 2023/0001044 A1 Jan. 5, 2023

Related U.S. Application Data

(63) Continuation-in-part of application No. 17/340,313, filed on Jun. 7, 2021, now Pat. No. 11,384,260.

(60) Provisional application No. 63/194,297, filed on May 28, 2021.

(51) Int. Cl.

| | |
|---|---|
| ***A61L 24/00*** | (2006.01) |
| ***A61L 24/04*** | (2006.01) |
| ***C08L 101/12*** | (2006.01) |
| ***C08L 101/16*** | (2006.01) |

(52) U.S. Cl.
CPC ......... *A61L 24/0042* (2013.01); *A61L 24/046* (2013.01); *C08L 101/12* (2013.01); *C08L 101/16* (2013.01)

(58) Field of Classification Search
CPC .. A61L 24/0042; A61L 24/046; C08L 101/12; C08L 101/16
See application file for complete search history.

(56) References Cited

U.S. PATENT DOCUMENTS

| | | | |
|---|---|---|---|
| 3,480,492 | A | 11/1969 | Hauser |
| 5,266,608 | A | 11/1993 | Katz et al. |
| 5,749,895 | A | 5/1998 | Sawyer et al. |
| 6,066,176 | A | 5/2000 | Oshida |
| 6,486,232 | B1 | 11/2002 | Wise et al. |
| 6,666,870 | B2 | 12/2003 | Dixon et al. |
| 7,066,962 | B2 | 6/2006 | Swords |
| 7,335,210 | B2 | 2/2008 | Smit |

(Continued)

FOREIGN PATENT DOCUMENTS

| | | | |
|---|---|---|---|
| CA | 2268478 | A1 | 2/1999 |
| CA | 2656681 | A1 | 2/2008 |

(Continued)

OTHER PUBLICATIONS

International Search Report and Written Opinion for International Application No. PCT/CA2022/050844, mailed Aug. 30, 2022 (18 pages).

(Continued)

*Primary Examiner* — Sameh R Boles
(74) *Attorney, Agent, or Firm* — Clark & Elbing LLP

(57) ABSTRACT

The invention features adhesive devices for holding objects (e.g., bone fragments) fixed with respect to each other.

18 Claims, 2 Drawing Sheets

(56) References Cited

U.S. PATENT DOCUMENTS

| | | | |
|---|---|---|---|
| 7,842,146 B2 | 11/2010 | Siavoshani et al. | |
| 7,967,820 B2 | 6/2011 | Bonutti et al. | |
| 8,119,742 B2 | 2/2012 | Dalsin et al. | |
| 8,221,475 B2 | 7/2012 | Aeschlimann et al. | |
| 8,398,720 B2 | 3/2013 | Swords | |
| 8,403,968 B2 | 3/2013 | Rabiner et al. | |
| 8,431,226 B2 | 4/2013 | Huerta et al. | |
| 8,673,354 B2 | 3/2014 | Bianco-Peled et al. | |
| 8,754,285 B2 | 6/2014 | Lee et al. | |
| 8,815,973 B2 | 8/2014 | Lin et al. | |
| 8,893,790 B2 | 11/2014 | Reyes et al. | |
| 8,916,652 B2 | 12/2014 | Dalsin et al. | |
| 8,962,772 B2 | 2/2015 | Ding et al. | |
| 8,968,716 B2 | 3/2015 | Park et al. | |
| 9,163,169 B2 | 10/2015 | Balogh et al. | |
| 9,228,112 B2 | 1/2016 | Gorodisher et al. | |
| 9,260,641 B2 | 2/2016 | Fant | |
| 9,283,298 B2 | 3/2016 | Nagatomi et al. | |
| 9,296,843 B2 | 3/2016 | Messersmith et al. | |
| 9,303,048 B2 | 4/2016 | Hirokami | |
| 9,332,991 B2 | 5/2016 | Pereira et al. | |
| 9,370,385 B2 | 6/2016 | Weinzweig | |
| 9,447,407 B2 | 9/2016 | Zink et al. | |
| 9,466,544 B2 | 10/2016 | Uehling | |
| 9,572,910 B2 | 2/2017 | Messersmith et al. | |
| 9,597,133 B2 | 3/2017 | McCarthy et al. | |
| 9,687,582 B2 | 6/2017 | Messersmith et al. | |
| 9,750,842 B2 | 9/2017 | Kourtis et al. | |
| 10,045,801 B2 | 8/2018 | Whyne et al. | |
| 10,646,264 B2 | 5/2020 | Whyne et al. | |
| 11,384,260 B1 | 7/2022 | Floros et al. | |
| 11,643,574 B2 | 5/2023 | Floros et al. | |
| 2004/0037906 A1 | 2/2004 | Li et al. | |
| 2005/0201974 A1 | 9/2005 | Schestopol et al. | |
| 2006/0045864 A1 | 3/2006 | Martensson et al. | |
| 2007/0173949 A1 | 7/2007 | Sharps et al. | |
| 2008/0169059 A1 | 7/2008 | Messersmith et al. | |
| 2008/0247984 A1 | 10/2008 | Messersmith et al. | |
| 2009/0024161 A1* | 1/2009 | Bonutti | A61B 17/7058 606/213 |
| 2009/0044895 A1 | 2/2009 | Fortune et al. | |
| 2009/0076241 A1 | 3/2009 | Lee | |
| 2009/0254006 A1 | 10/2009 | Babaev | |
| 2010/0137903 A1 | 6/2010 | Lee et al. | |
| 2010/0330025 A1 | 12/2010 | Messersmith et al. | |
| 2011/0086095 A1 | 4/2011 | Jacob et al. | |
| 2011/0105712 A1 | 5/2011 | Jiang et al. | |
| 2011/0172721 A1* | 7/2011 | Frigg | A61B 17/68 606/329 |
| 2012/0093895 A1 | 4/2012 | Song et al. | |
| 2012/0116424 A1 | 5/2012 | Lee et al. | |
| 2013/0023879 A1 | 1/2013 | Kerr et al. | |
| 2013/0052712 A1 | 2/2013 | Cha et al. | |
| 2013/0053898 A1 | 2/2013 | Voisard et al. | |
| 2013/0183630 A1 | 7/2013 | Krikorian et al. | |
| 2014/0058184 A1 | 2/2014 | Crawford | |
| 2014/0221485 A1 | 8/2014 | Gunther et al. | |
| 2014/0277399 A1 | 9/2014 | Pacetti et al. | |
| 2014/0311673 A1 | 10/2014 | Zhao et al. | |
| 2014/0315955 A1 | 10/2014 | Chung et al. | |
| 2015/0114261 A1 | 4/2015 | Thevasahayam | |
| 2015/0182670 A1 | 7/2015 | Rizk et al. | |
| 2015/0322243 A1 | 11/2015 | Jaerger et al. | |
| 2015/0361310 A1 | 12/2015 | Combs et al. | |
| 2016/0032047 A1 | 2/2016 | Murphy et al. | |
| 2016/0051296 A1* | 2/2016 | Weinzweig | A61L 31/06 606/280 |
| 2016/0160097 A1 | 6/2016 | Waite et al. | |
| 2016/0263136 A1 | 9/2016 | Cha et al. | |
| 2017/0056548 A1 | 3/2017 | Lee et al. | |
| 2017/0065495 A1 | 3/2017 | Eckert et al. | |
| 2017/0210852 A1 | 7/2017 | Becker et al. | |
| 2019/0022273 A1* | 1/2019 | Hess | A61B 17/70 |
| 2019/0038328 A1 | 2/2019 | Whyne et al. | |
| 2019/0224776 A1* | 7/2019 | Hirose | B29C 66/21 |
| 2019/0262276 A1 | 8/2019 | Zilberman et al. | |
| 2020/0373584 A1* | 11/2020 | Morin | H01M 50/534 |
| 2022/0395608 A1 | 12/2022 | Santerre et al. | |
| 2023/0001045 A1* | 1/2023 | Floros | A61L 24/0042 |
| 2023/0001046 A1 | 1/2023 | Santerre et al. | |
| 2023/0012485 A1* | 1/2023 | Santerre | A61L 24/046 |

FOREIGN PATENT DOCUMENTS

| | | | | |
|---|---|---|---|---|
| CA | 2751570 A1 | 8/2010 | | |
| CA | 2751572 A1 | 8/2010 | | |
| CA | 2777668 C | 2/2019 | | |
| CN | 106928672 A | 7/2017 | | |
| CN | 107868645 A | 4/2018 | | |
| DE | 10358779 A1 | 7/2005 | | |
| DE | 60118256 T2 | 12/2006 | | |
| EP | 1488753 A1 | 12/2004 | | |
| EP | 2614810 A2 | 7/2013 | | |
| JP | 2001-327520 A | 11/2001 | | |
| WO | WO-2005/056680 A1 | 6/2005 | | |
| WO | WO-2008/080239 A1 | 7/2008 | | |
| WO | WO-2009/029908 A1 | 3/2009 | | |
| WO | WO-2009/137190 A2 | 11/2009 | | |
| WO | WO-2011/048077 A2 | 4/2011 | | |
| WO | WO-2011/115420 A2 | 9/2011 | | |
| WO | WO-2012/004570 A2 | 1/2012 | | |
| WO | WO-2012/064821 A2 | 5/2012 | | |
| WO | WO-2014/019083 A1 | 2/2014 | | |
| WO | WO-2014/118266 A1 | 8/2014 | | |
| WO | WO-2014/138190 A1 | 9/2014 | | |
| WO | WO-2014/195169 A1 | 12/2014 | | |
| WO | WO-2016/010484 A1 | 1/2016 | | |
| WO | WO-2016/049029 A1 | 3/2016 | | |
| WO | WO-2017/004174 A1 | 1/2017 | | |
| WO | WO-2017044896 A1 * | 3/2017 | | C09J 135/00 |
| WO | WO-2017/095782 A1 | 6/2017 | | |
| WO | WO-2021/119853 A1 | 6/2021 | | |
| WO | WO-2021/119854 A1 | 6/2021 | | |
| WO | WO-2021/119855 A1 | 6/2021 | | |

OTHER PUBLICATIONS

Office Action for U.S. Appl. No. 17/338,951, mailed Oct. 14, 2021 (15 pages).

Office Action for U.S. Appl. No. 17/340,313, mailed Nov. 9, 2021 (7 pages).

Response to Non-Final Office Action for U.S. Appl. No. 17/338,951, dated Jan. 10, 2022 (8 pages).

* cited by examiner

ADHESIVE DEVICES AND USES THEREOF

BACKGROUND

Surgical adhesives designed to interface with tissues, especially for internal use, must be biocompatible, easy to apply, and able to adhere to biological tissues under wet, dry, clean and/or biofouled conditions. These requirements, however, greatly limit the application of surgical adhesives in biomedical applications, with current commercially available surgical adhesives presenting one or more of undesirable strength, toxicity, difficult workflow, and/or requiring clean, dry surfaces for optimal performance.

Severe traumatic craniomaxillofacial (CMF) fracture commonly occurs due to high energy trauma such as motor vehicle accidents, sports injuries, war injuries, and physical assault. Many of these fractures require surgical stabilization and/or reconstructed. Current adhesives that may be used to stabilize CMF and other fractures suffer from one or more of the following deficiencies: high water solubility, weak bond strength, a curing time that is either too slow or too fast, irreversible rigid curing that does not allow proper reduction, and a lack of biocompatibility. Therefore, there exists a need for new bioadhesives.

SUMMARY OF THE INVENTION

The invention features adhesive devices for holding objects (e.g., bone fragments) fixed in position with respect to each other.

In a first aspect, the invention features a method for stabilizing bone fragments in a body, the method including the steps of:

(i) forming a first anchor on a first bone fragment by (a) heating an adhesive composition to form a softened adhesive composition and contacting the softened adhesive composition to the first bone fragment, and (b) permitting the softened adhesive composition to cool to form the first anchor affixed to the first bone fragment;

(ii) forming a second anchor on a second bone fragment by (a) heating an adhesive composition to form a softened adhesive composition and contacting the softened adhesive composition to the second bone fragment, and (b) permitting the softened adhesive composition to cool to form the second anchor affixed to the second bone fragment;

wherein the adhesive composition has a tackifying temperature of at least 40° C. (e.g., at least 42° C., at least 45° C., at least 50° C., at least 55° C., or between from 40° C. to 55° C.), and wherein the first anchor and the second anchor are connected to a support structure for stabilizing the bone fragments.

In some embodiments, the support structure is a flexible support including a biodegradable and biocompatible polymer linking the first anchor to the second anchor. In some embodiments, the support structure, the first anchor, and the second anchor are formed from a tape including (x) a non-adhesive top layer that is the support structure, and (y) a bottom layer that is adhesive when softened to form the first anchor and the second anchor.

In some embodiments, the adhesive composition is not water soluble (e.g., has a water solubility at 25° C. of less than 30 mg/L, 25 mg/L, 20 mg/L, or 15 mg/L). In other embodiments, the adhesive composition is water soluble (e.g., has a solubility in water at 25° C. of greater than 30 mg/L or 50 mg/L).

In some embodiments, the adhesive composition includes an inorganic particulate additive heat transfer agent. In some embodiments, the heat transfer agent (e.g., sodium chloride, iron(III) phosphate dihydrate, iron(III) citrate monohydrate, hydroxyapatite, tetracalcium phosphate, tricalcium phosphate, dicalcium phosphate, and sodium carbonate, or a combination thereof (e.g., hydroxyapatite)) is present in an amount that permits the softened adhesive composition to cool and harden in 120 seconds or less (e.g., 10 seconds or less). In some embodiments, the heat transfer agent is present in an amount that permits the adhesive composition to soften within 120 seconds or less of applying energy (e.g., within 10 seconds or less). In particular embodiments, the heat transfer agent is present in an amount that permits the adhesive composition to soften within 10 seconds or less of applying energy to the non-adhesive top layer. In some embodiments, the adhesive composition includes about 0.5-60% (w/w) heat transfer agent (e.g., 7.5±2.5%, 10±5%, 15±5%, 20±5%, 25±10%, 37.5±5%, 50±10%, or 35-60% (w/w)).

In some embodiments of the second aspect, the adhesive layer includes a particulate filler. In some embodiments, the particulate filler prevents loss of the adhesive composition upon heating. In some embodiments, the particulate filler is insoluble.

In some embodiments, the adhesive composition includes a polymer having the structure of formula (I):

formula (I)

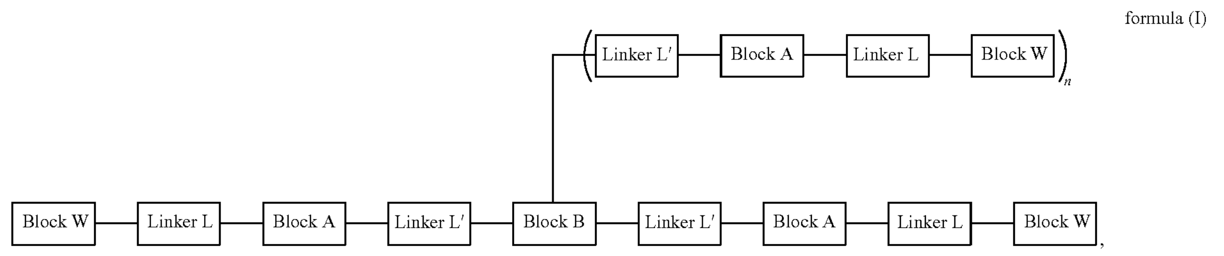

wherein n is an integer from 0 to 4 (e.g., n=1, 2, 3, or 4);

Block B includes an oligomer derived from a polyester, polyether, polalkylene glycol, polysilicone, or polycarbonate with a MW<10,000 g/mol (e.g., 2±1 KDa, 4±2 KDa, 5±2.5 KDa, or 8±2 KDa);

Block A includes an optionally substituted $C_1$-$C_6$ alkylene, wherein Block A is derived from a diisocyanate crosslinker;

Block W includes an optionally substituted $C_0$-$C_3$ alkyl-benzene-diol or optionally substituted $C_0$-$C_3$ alkyl-benzene-triol;

Linker L' includes a carbamate; and

Linker L includes a urea.

In some embodiments, Block B includes an oligomer derived from a polyester, polalkylene glycol, polysilicone, or polycarbonate. In particular embodiments, the Block B oligomer has a MW 4,000 g/mol (e.g., 1±0.5 KDa, 2±0.5 KDa, or 3±1 KDa).

In some embodiments, Block B has the structure of formula (II):

formula (II)

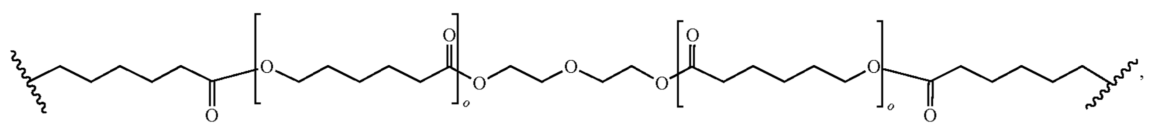

wherein each o is, independently, an integer from 0 to 20 (e.g., n=0-4, 2-6, 4-10, 5-15, or 10-20).

In some embodiments, Block B has the structure of formula (III):

formula (III)

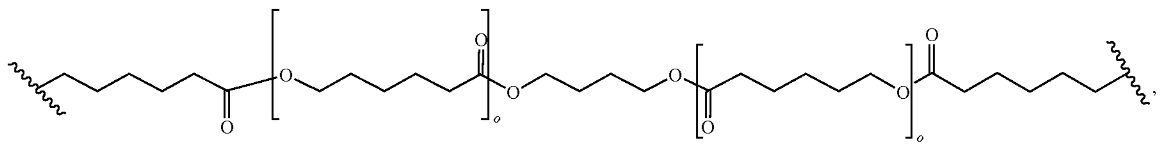

wherein each o is, independently, an integer from 0 to 20 (e.g., n=0-4, 2-6, 4-10, 5-15, or 10-20).

In some embodiments, Block B has the structure of formula (IV):

formula (IV)

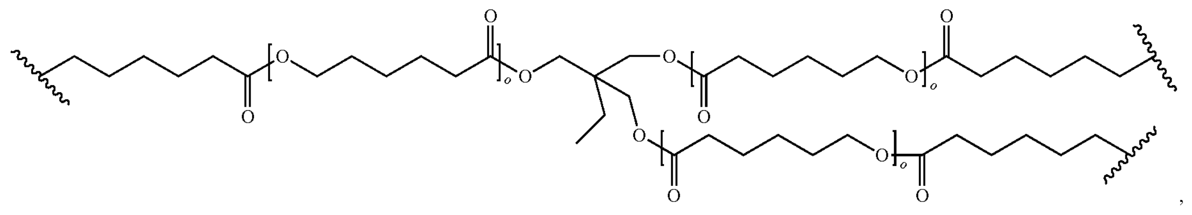

wherein each o is, independently, an integer from 0 to 20 (e.g., n=0-4, 2-6, 4-10, 5-15, or 10-20).

In some embodiments, Block B has the structure of formula (V)

formula (V)

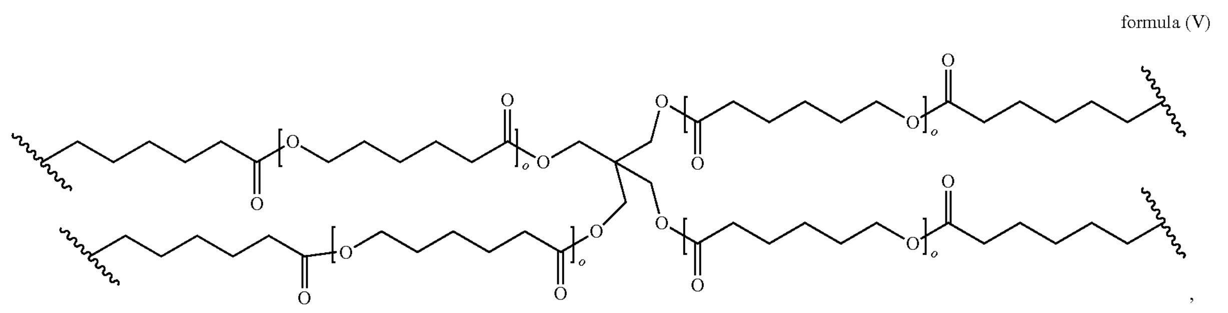

wherein each o is, independently, an integer from 0 to 20 (e.g., n=0-4, 2-6, 4-10, 5-15, or 10-20).

In some embodiments, Block B has the structure of formula (VI):

formula (VI)

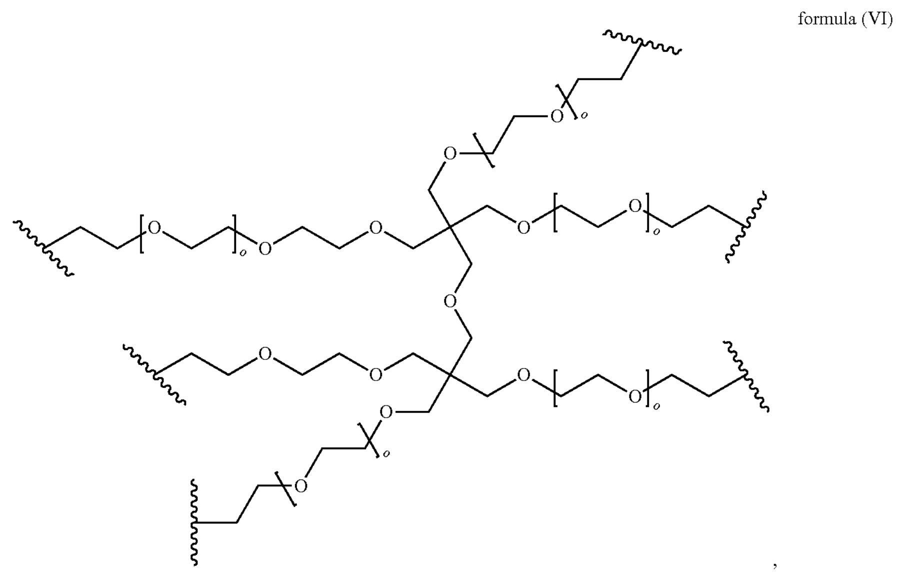

wherein each o is, independently, an integer from 0 to 20 (e.g., n=0-4, 2-6, 4-10, 5-15, or 10-20).

In some embodiments, Block A has the structure of formula (VII):

formula (VII)

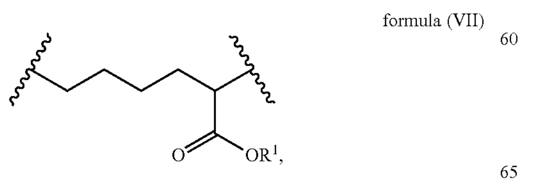

wherein $R^1$ is $C_1$-$C_3$ alkyl.

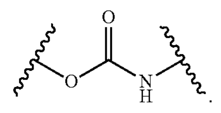 [SMILES: *NC(=O)O*]

In some embodiments, Linker L' has the structure:

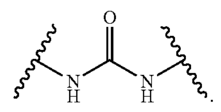 [SMILES: *NC(=O)N*]

In some embodiments, Linker L has the structure:

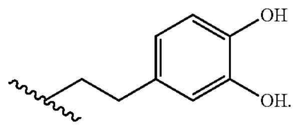 [SMILES: *CCc1ccc(O)c(O)c1]

In some embodiments, Block W has the structure:

In some embodiments, the adhesive composition includes from 30-70% (w/w) of a filler.

In some embodiments, the filler includes polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), hydroxyapatite (HA), tetracalcium phosphate (TTCP), tricalcium phosphate (TCP), dicalcium phosphate (DCP) or a copolymer thereof, or a blend thereof. In some embodiments, the filler includes polycaprolactone (PCL), polydioxanone (PDX), poly(lactic-co-glycolic acid) (PLGA), or poly-3-hydroxybutyrate (P3HB), or a copolymer thereof, or a blend thereof.

In some embodiments, step (i) and step (ii) are repeated to stabilize a plurality of bone fragments in a subject. In some embodiments, from 2 to 5, 6 to 10, 11 to 15, 16 to 20, 21 to 25, 26 to 30, 31 to 35, 36 to 40, 41 to 45, 46 to 50 or more bone fragments are stabilized in a subject.

In an embodiment of any of the above methods, the heating includes applying an energy source. For example, the energy source can be ultrasonic energy, or any other energy source described herein. In certain embodiments, the ultrasonic energy is applied at a frequency of from 35 kHz to 70 kHz (e.g., 45±10 kHz, 55±10 kHz, or 60±10 kHz, or 70 kHz), optionally from 1.5 to 5.0 J of energy is applied (e.g., 2.0±0.5 J, 3.0±0.5 J, 4.0±0.5 J, or 4.5±0.5 J). In particular embodiments, the ultrasonic energy is applied at a frequency and with an amount sufficient to displace fluids between the adhesive composition and the bone fragment prior to the formation of the first anchor and the second anchor. The ultrasonic energy can be applied using an ultrasonic welder. In certain embodiments, the ultrasonic welder includes a horn tip with individual texture elements, and wherein the individual texture elements are evenly spaced apart with uniform depths of up to 0.127 mm.

In an embodiment of any of the above methods, the method includes one or more of the following features: (i) reversibly stabilizing bone fragments; (ii) the first anchor and the second anchor are reversible anchors; (iii) the adhesive composition is not dependent upon in situ curing reactions for adhesion; and/or (iv) the adhesive composition is reversibly softening at a temperature of 45±5° C. or 55±5° C.

In an embodiment of any of the above methods, the support structure, the first anchor, and the second anchor are formed from a tape including (x) a non-adhesive top layer that is the support structure, and (y) a bottom layer that is adhesive when softened to form the first anchor and the second anchor.

In an embodiment of any of the above methods, (i) the support structure and (ii) at least one of the first anchor and the second anchor are arranged to form an adhesive portion and a support portion that forms a backing to the adhesive portion, and wherein the adhesive portion when heated is capable of softening without deformation of the support portion. The backing portion can have a thickness of from 0.05 to 0.31 mm. In some embodiments, the backing portion has a thickness of from 0.12 to 0.20 mm. The adhesive portion can have a thickness of from 0.05 to 0.16 mm. In some embodiments, the adhesive portion has a thickness of 0.075±0.025 mm or 0.13±0.03 mm.

In some embodiments, the heating includes application with a welder via a series of consecutive welding tacks normal to the application surface so as to cover the entire surface. In some embodiments, the heating includes continuous sliding of a welder across the entirety of the device surface in a brushstroke or painting motion.

In a second aspect, the invention features a device for stabilizing bone fragments in a body, the device including:

(i) a first anchor capable of affixing to a first bone fragment, the first anchor including an adhesive composition that softens with heating and forms the first anchor upon cooling;

(ii) a second anchor capable of affixing to a second bone fragment, the second anchor including an adhesive composition that softens with heating and forms the second anchor upon cooling;

(iii) a support structure connecting the first anchor to the second anchor capable of stabilizing the bone fragments;

wherein the adhesive composition has a tackifying temperature of at least 40° C. (e.g., at least 42° C., at least 45° C., at least 50° C., at least 55° C., or between from 40° C. to 55° C.).

In some embodiments of the second aspect, the support structure is a flexible support including a biodegradable and biocompatible polymer linking the first anchor to the second anchor. In some embodiments, the support structure, the first anchor, and the second anchor are formed from a tape including (x) a non-adhesive top layer that is the support structure, and (y) a bottom layer that is adhesive when softened to form the first anchor and the second anchor.

In some embodiments of the second aspect, the adhesive composition is not water soluble.

In some embodiments of the second aspect, the adhesive composition includes a heat transfer agent. In some embodiments, the heat transfer agent is an inorganic particulate additive heat transfer agent. In some embodiments, the heat transfer agent (e.g., sodium chloride, iron(III) phosphate dihydrate, iron(III) citrate monohydrate, hydroxyapatite, tetracalcium phosphate, tricalcium phosphate, dicalcium phosphate, and sodium carbonate, or a combination thereof (e.g., hydroxyapatite)) is present in an amount that permits the softened adhesive composition to cool and harden in 120 seconds or less (e.g., within 10 seconds or less). In some embodiments, the heat transfer agent is present in an amount that permits the adhesive composition to soften within 120 seconds or less of applying energy (e.g., within 10 seconds or less). In some embodiments, the heat transfer agent includes about 0.5-60% (w/w) of the adhesive composition (e.g., 7.5±2.5%, 10±5%, 15±5%, 20±5%, 25±10%, 37.5±5%, 50±10%, or 35-60% (w/w)).

In some embodiments of the second aspect, the adhesive layer includes a particulate filler. In some embodiments, the particulate filler prevents loss of the adhesive composition upon heating. In some embodiments, the particulate filler is insoluble.

In some embodiments of the second aspect, the adhesive composition includes a polymer having the structure of formula (I):

formula (I)

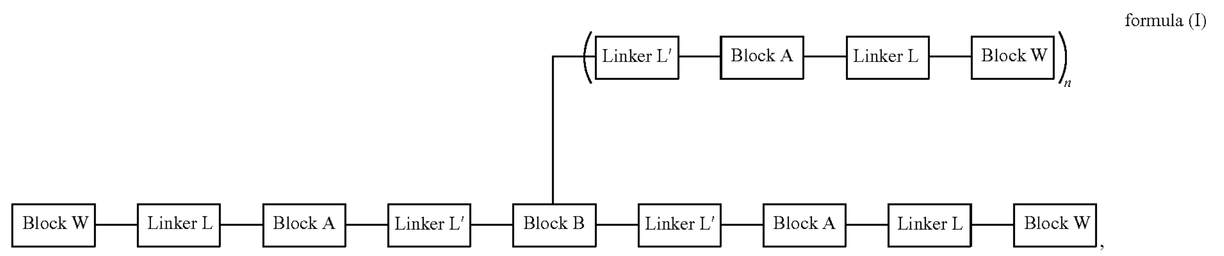

wherein n is an integer from 0 to 4 (e.g., n=1, 2, 3, or 4);

Block B includes an oligomer derived from a polyester, polyether, polalkylene glycol, polysilicone, or polycarbonate with a MW<10,000 g/mol (e.g., 2±1 KDa, 4±2 KDa, 5±2.5 KDa, or 8±2 KDa);

Block A includes an optionally substituted $C_1$-$C_6$ alkylene, wherein Block A is derived from a diisocyanate crosslinker;

Block W includes an optionally substituted $C_0$-$C_3$ alkylbenzene-diol or optionally substituted $C_0$-$C_3$ alkylbenzene-triol;

Linker L' includes a carbamate; and

Linker L includes a urea.

In some embodiments, Block B includes an oligomer derived from a polyester, polalkylene glycol, polysilicone, or polycarbonate. In particular embodiments, the Block B oligomer has a MW 4,000 g/mol (e.g., 1±0.5 KDa, 2±0.5 KDa, or 3±1 KDa).

In some embodiments of the second aspect of the invention, Block B has the structure of formula (II):

formula (II)

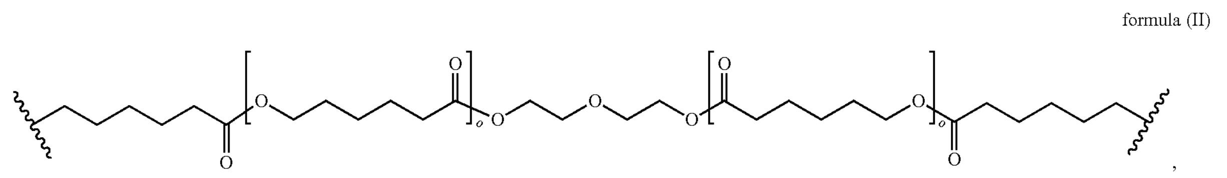

wherein each o is, independently, an integer from 0 to 20 (e.g., n=0-4, 2-6, 4-10, 5-15, or 10-20).

In some embodiments of the second aspect of the invention, Block B has the structure of formula formula (III)

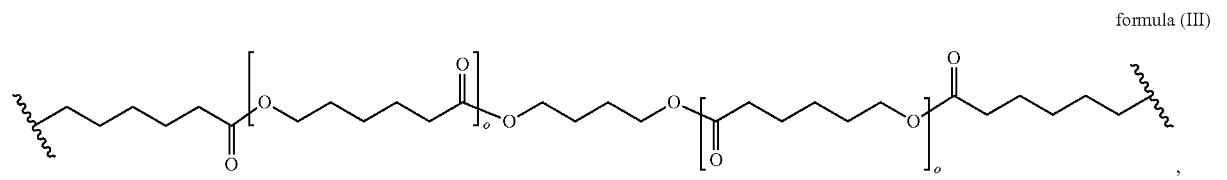

wherein each o is, independently, an integer from 0 to 20 (e.g., n=0-4, 2-6, 4-10, 5-15, or 10-20).

In some embodiments of the second aspect of the invention, Block B has the structure of formula (IV):

formula (IV)

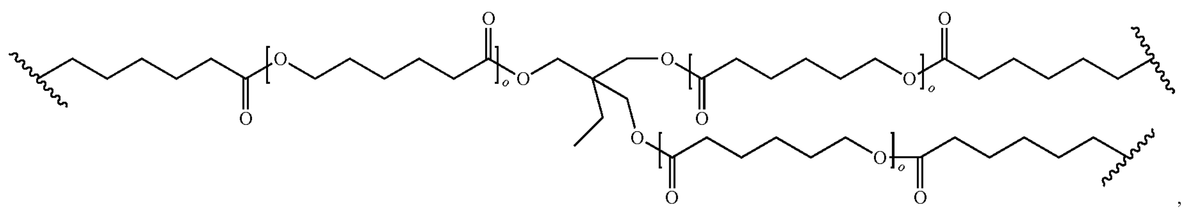

wherein each o is, independently, an integer from 0 to 20 (e.g., n=0-4, 2-6, 4-10, 5-15, or 10-20).

In some embodiments of the second aspect of the invention, Block B has the structure of formula (V)

formula (V)

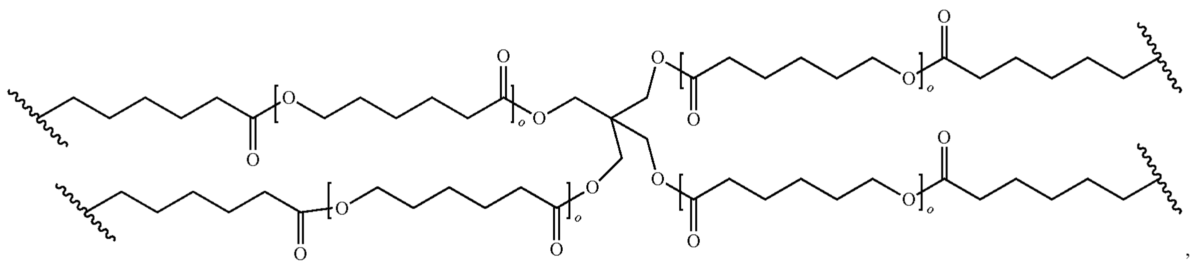

wherein each o is, independently, an integer from 0 to 20 (e.g., n=0-4, 2-6, 4-10, 5-15, or 10-20).

In some embodiments of the second aspect of the invention, Block B has the structure of formula (VI):

formula (VI)

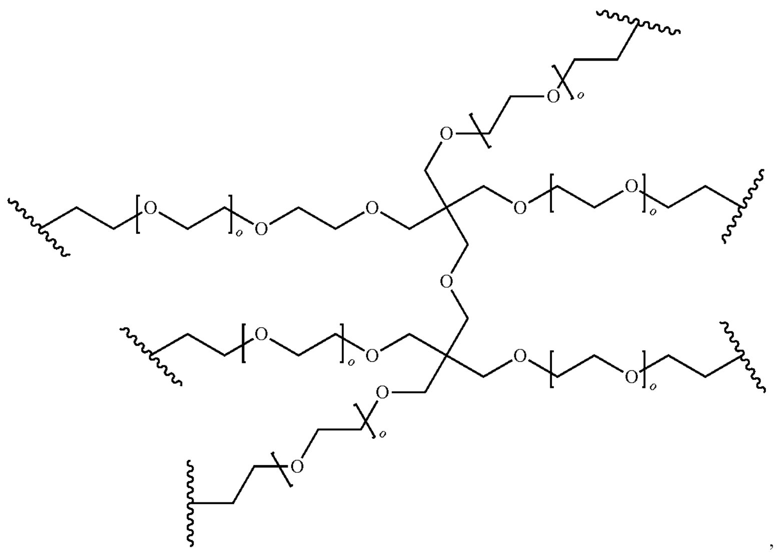

wherein each o is, independently, an integer from 0 to 20 (e.g., n=0-4, 2-6, 4-10, 5-15, or 10-20).

In some embodiments of the second aspect of the invention, Block A has the structure of formula (VII):

formula (VII)

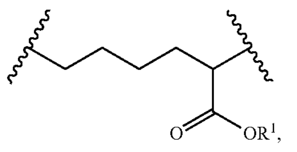

wherein $R^1$ is $C_1$-$C_3$ alkyl.

In some embodiments of the second aspect of the invention, Linker L' has the structure:

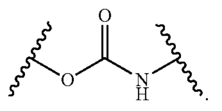 [SMILES: *NC(=O)O*]

In some embodiments of the second aspect of the invention, Linker L has the structure:

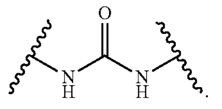 [SMILES: *NC(=O)N*]

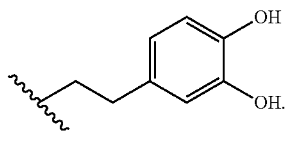 [SMILES: *CCc1ccc(O)c(O)c1]

or a copolymer thereof, or a blend thereof. In certain embodiments, the filler includes hydroxyapatite (HA).

In some embodiments of the second aspect of the invention, the device includes a plurality of bone anchors and a plurality of support structures capable of stabilizing a plurality of bone fragments in a subject.

In an embodiment of any of the above devices, (i) the support structure and (ii) at least one of the first anchor and the second anchor are arranged to form an adhesive portion and a support portion that forms a backing to the adhesive portion, and wherein the adhesive portion when heated is capable of softening without deformation of the support portion. The backing portion can have a thickness of from 0.05 to 0.31 mm. In some embodiments, the backing portion has a thickness of from 0.12 to 0.20 mm. The adhesive portion can have a thickness of from 0.05 to 0.16 mm. In some embodiments, the adhesive portion has a thickness of 0.075±0.025 mm or 0.13±0.03 mm.

In an embodiment of any of the above devices, the device includes one or more of the following features: (i) the first anchor and the second anchor are each capable of affixing to wet or dry bone fragments; (ii) the first anchor and the second anchor are reversible anchors; (iii) the adhesive composition is not dependent upon in situ curing reactions for adhesion; and/or (iv) the adhesive composition is reversibly softening at a temperature of 45±5° C. or 55±5° C.

In a third aspect, the invention features an adhesive composition including:

(i) from 0-70% (w/w) of a filler; and (ii) from 30-100% (w/w) of a polymer (e.g., 30-35% (w/w)) having the structure of formula (I):

formula (I)

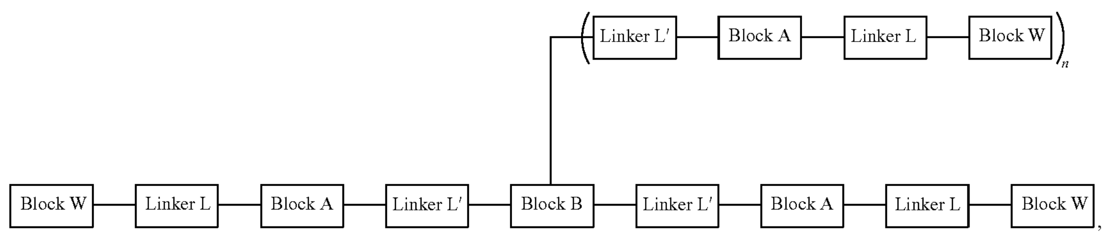

In some embodiments of the second aspect, Block W has the structure:

In some embodiments of the second aspect of the invention, the adhesive composition includes from 30-70% (w/w) of a filler (e.g., polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly (trimethylene carbonate) (PTMC), polysulfone, polyethylene glycol (PEG), hydroxyapatite (HA), tetracalcium phosphate (TTCP), tricalcium phosphate (TCP), dicalcium phosphate (DCP), or a copolymer thereof, or a blend thereof). In some embodiments, the filler includes polycaprolactone (PCL), polydioxanone (PDX), poly(lactic-co-glycolic acid) (PLGA), or poly-3-hydroxybutyrate (P3HB), wherein n is an integer from 0 to 4 (e.g., n=1, 2, 3, or 4);

Block B includes an oligomer derived from a polyester, polyether, polalkylene glycol, polysilicone, or polycarbonate with a MW<10,000 g/mol (e.g., 2±1 KDa, 4±2 KDa, 5±2.5 KDa, or 8±2 KDa);

Block A includes an optionally substituted $C_1$-$C_6$ alkylene, wherein Block A is derived from a diisocyanate crosslinker;

Block W includes an optionally substituted $C_0$-$C_3$ alkylbenzene-diol or optionally substituted $C_0$-$C_3$ alkylbenzene-triol;

Linker L' includes a carbamate; and

Linker L includes a urea, wherein the adhesive composition has a tackifying temperature of at least 40° C. (e.g., at least 42° C., at least 45° C., at least 50° C., at least 55° C., or between from 40° C. to 55° C.).

In some embodiments, Block B includes an oligomer derived from a polyester, polalkylene glycol, polysilicone, or polycarbonate. In particular embodiments, the Block B oligomer has a MW 4,000 g/mol (e.g., 1±0.5 KDa, 2±0.5 KDa, or 3±1 KDa).

In some embodiments of the third aspect, the adhesive composition is not water soluble.

In some embodiments of the third aspect, the adhesive composition includes a heat transfer agent (e.g., sodium chloride, iron(III) phosphate dihydrate, iron(III) citrate monohydrate, hydroxyapatite, tetracalcium phosphate, tricalcium phosphate, dicalcium phosphate, sodium carbonate, or a combination thereof (e.g., hydroxyapatite)). In some embodiments, the heat transfer agent is present in an amount that permits the softened adhesive composition to cool and harden in 120 seconds or less (e.g., 10 seconds or less). In some embodiments, the heat transfer agent is present in an amount that permits the adhesive composition to soften within 120 seconds or less of applying energy (e.g., 10 seconds or less). In some embodiments, the heat transfer agent includes about 0.5-60% (w/w) of the adhesive composition (e.g., 7.5±2.5%, 10±5%, 15±5%, 20±5%, 25±10%, 37.5±5%, 50±10%, or 35-60% (w/w)).

In some embodiments of the third aspect, Block B has the structure of formula (II):

formula (II)

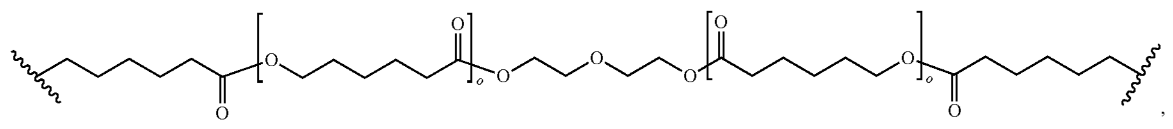

wherein each o is, independently, an integer from 0 to 20 (e.g., n=0-4, 2-6, 4-10, 5-15, or 10-20).

In some embodiments of the third aspect, Block B has the structure of formula (III):

formula (III)

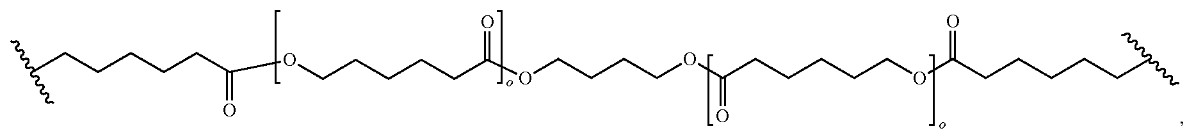

wherein each o is, independently, an integer from 0 to 20 (e.g., n=0-4, 2-6, 4-10, 5-15, or 10-20).

In some embodiments of the third aspect, Block B has the structure of formula (IV):

formula (IV)

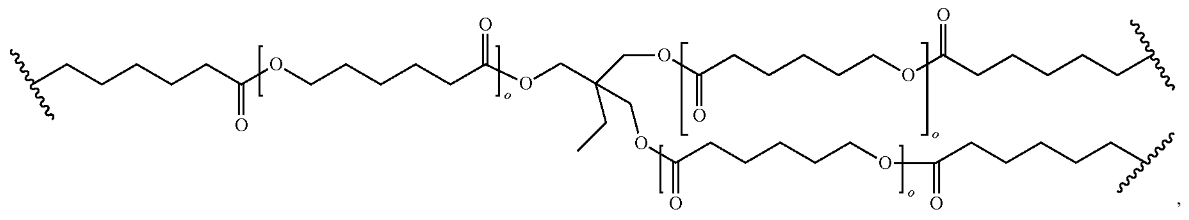

wherein each o is, independently, an integer from 0 to 20 (e.g., n=0-4, 2-6, 4-10, 5-15, or 10-20).

In some embodiments of the third aspect, Block B has the structure of formula (V)

formula (V)

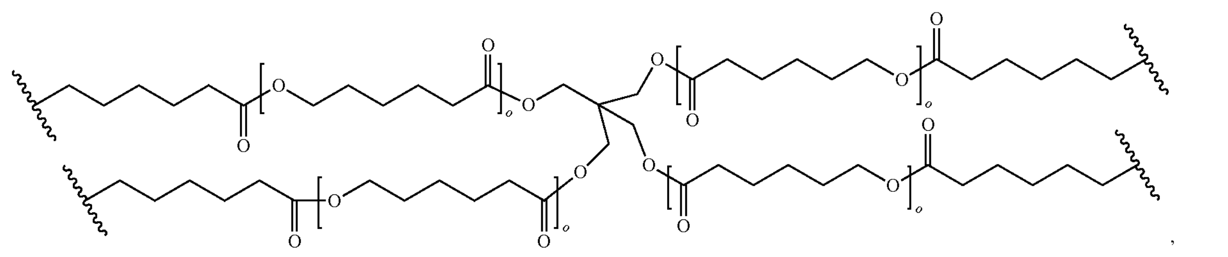

wherein each o is, independently, an integer from 0 to 20 (e.g., n=0-4, 2-6, 4-10, 5-15, or 10-20).

In some embodiments of the third aspect, Block B has the structure of formula (VI):

formula (VI)

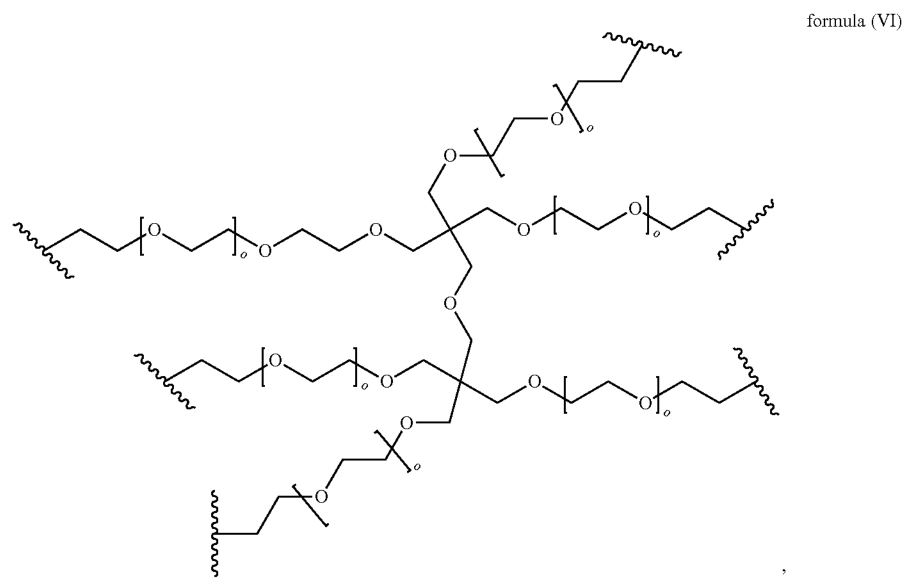

wherein each o is, independently, an integer from 0 to 20 (e.g., n=0-4, 2-6, 4-10, 5-15, or 10-20).

In some embodiments of the third aspect, Block A has the structure of formula (VII):

formula (VII)

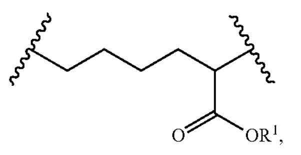

wherein $R^1$ is $C_1$-$C_3$ alkyl.

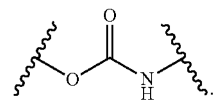 [SMILES: *NC(=O)O*]

In some embodiments of the third aspect, Linker L' has the structure:

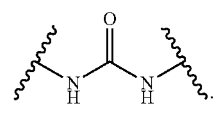 [SMILES: *NC(=O)N*]

In some embodiments of the third aspect, Linker L has the structure:

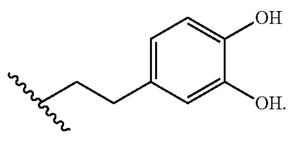 [SMILES: *CCc1ccc(O)c(O)c1]

In some embodiments of the third aspect, Block W has the structure:

In some embodiments of the third aspect, the filler includes polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), hydroxyapatite (HA), tetracalcium phosphate (TTCP), tricalcium phosphate (TCP), dicalcium phosphate (DCP), or a copolymer thereof, or a blend thereof. In some embodiments, the filler includes polycaprolactone (PCL), polydioxanone (PDX), poly(lactic-co-glycolic acid) (PLGA), or poly-3-hydroxybutyrate (P3HB), or a copolymer thereof, or a blend thereof. In certain embodiments, the filler comprises hydroxyapatite (HA).

In a fourth aspect, the invention features a tape including (i) a non-adhesive polymeric top layer, and (ii) a bottom layer including the adhesive composition of any one of the preceding embodiments.

In an embodiment of the layered tape, (i) the support structure and (ii) at least one of the first anchor and the second anchor are arranged to form an adhesive portion and a support portion that forms a backing to the adhesive portion, and wherein the adhesive portion when heated is capable of softening without deformation of the support portion. The backing portion can have a thickness of from 0.05 to 0.31 mm. In some embodiments, the backing portion has a thickness of from 0.12 to 0.20 mm. The adhesive portion can have a thickness of from 0.05 to 0.16 mm. In some embodiments, the adhesive portion has a thickness of 0.075±0.025 mm or 0.13±0.03 mm. In an embodiment of the layered tape, the tape includes one or more of the following features: (i) the first anchor and the second anchor are each capable of affixing to wet or dry bone fragments; (ii) the first anchor and the second anchor are reversible anchors; (iii) the adhesive composition is not dependent upon in situ curing reactions for adhesion; and/or (iv) the adhesive composition is reversibly softening at a temperature of 45±5° C. or 55±5° C.

In some embodiments of the fourth aspect, the non-adhesive polymeric top layer includes polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), or a copolymer thereof.

In a fourth aspect, the invention features a method of manufacturing the device of the invention or the tape of the invention, the method including: a) contacting (i) a first portion including an adhesive composition of the invention with (ii) a second portion including a support structure; and b) applying heat to join the first portion and the second portion. In certain embodiments, the method further includes applying a force to compress the first portion and the second portion. For example, a force of at least 800 kg can be applied. In some embodiments, the first portion and the second portion are joined by lamination. In particular embodiments, one or both of the first portion and the second portion is in the form of a sheet.

Definitions

As used herein, the term "about" represents a value that is in the range of ±10% of the value that follows the term "about."

The term "adhesion section," as used herein, refers to a portion of a device of the disclosure containing an adhesive composition. For example, the adhesion section in the device of the invention can be composed of 30-100% (w/w) of one or more of an adhesive composition (e.g., a polymer having the structure of formula (I) described herein), 0-70% (w/w) of one or more of a filler (e.g., a non-adhesive polymer), and 0.5-60% (w/w) of one or more of a heat transfer agent. The adhesion section adheres to at least one of the objects (e.g., a bone fragment). The adhesion section may also be one side of the device (e.g., the adhesion side).

As used herein, the term "adhesion side" refers to a coating or layer that is included of the following: 1) one or more of an adhesive (e.g., preferably a plurality of adhesives); 2) one or more of a filler; and 3) one or more of a heat transfer agent. The adhesion side can be softened upon exposure to energy such as, e.g., ultrasonic energy, infrared radiation, radiofrequency (RF)).

As used herein, the term "adhesive composition" refers compounds and blends that can adhesively affix one or more objects or materials together. The adhesive composition can be a polymer having the structure of formula (I), as described herein.

As used herein, the term "biocompatible" means the material will have no adverse effects on cells, tissue, or function in vivo for the indicated use, or conform to limits specified by internationally recognized testing standards governing biocompatible materials for medical applications.

As used herein, the term "biodegradable" means the material is capable of being broken down especially into innocuous products by the action of living things (e.g., the in vivo physiological environment). A biodegradable material may be hydrolysable or enzyme degradable.

The term, "filler," as used herein, refers to a non-adhesive material or substance that may be added to alter properties including, but not limited to, adhesion strength, tackifying temperature, cytotoxicity, tensile strength, time of rigidification, and viscosity. For example, a filler can be, e.g., polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), hydroxyapatite (HA), tetracalcium phosphate (TTCP), tricalcium phosphate (TCP), dicalcium phosphate (DCP), or a copolymer thereof.

As used herein, the term "heat transfer agent" is compound that accelerates the formation of a softened adhesive. A heat transfer agent may be a salt, such as, e.g., sodium chloride, iron(III) phosphate dihydrate, iron(III) citrate monohydrate, hydroxyapatite, tetracalcium phosphate (TTCP), tricalcium phosphate (TCP), dicalcium phosphate (DCP), or sodium carbonate.

As used herein, the term "rigidify" refers to an increase in the stiffness of the material or substance. For example, an adhesion section (or adhesion side) of the disclosure can be softened after exposure to energy (e.g., within 120 seconds or less (e.g., within 10 seconds or less)); the adhesion section (or adhesion side) may then rigidify (i.e., stiffen) within 120 seconds or less (e.g., within 10 seconds or less). The rigidification of the adhesion section (or adhesion side) which fixes two (or more) bone fragments with respect to each other allows bone fractures to heal.

As used herein, the term "soften" refers to a decrease in the stiffness of the material or substance. For example, a device or an adhesion side of the disclosure can soften after exposure to energy; within 120 seconds or less (e.g., 10 seconds or less), the softened adhesion side can flow, conforming to the geometry of a biological tissue or other substrate.

As used herein, the term "tackifying temperature" refers to a temperature at which an adhesive blend or compound goes from non-flowable to string forming when contacted with a glass pipette tip. The adhesive blend or compound may decrease in stiffness (e.g., a reversible phase transition temperature). For example, a device or an adhesion side of the disclosure can soften once it reaches the tackifying temperature (e.g., the device or the adhesion side of the disclosure).

The term "subject," as used herein, refers to a human or non-human animal (e.g., a mammal such as a non-human primate, horse, cow, pig, or dog).

As used herein, the term "support structure" refers to a portion of a device of the disclosure that physically supports an adhesive section. For example, the device of the invention can be composed of 40-100% of one or more of a non-adhesive polymer (e.g., as a support). The support structure can be found between two adhesion sections. For example, the support structure can be one side of the device (e.g., the support side).

As used herein, the term "support side" refers to a support structure positioned as a backing for the adhesion side of a device of the invention. The support side can be formed from one or more non-adhesive polymers, such as, e.g., polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), or a copolymer thereof. For example, when the device is a bone tape, the support side can form a non-adhesive backing that structurally supports adhesion sections on the sticky side of the bone tape.

As used herein, the term "surface fouling" refers to an adhesive or admixture of two or more adhesives losing the ability to adhere to a surface in the presence of an aqueous liquid (e.g., water, blood, serum, plasma). The adhesion sections in the devices of the invention can be formulated to resist surface fouling.

The term "water soluble," as used herein, refers to a material or substance that may dissolve in water. A material or substance that is "not water soluble" (e.g., an adhesion section (or adhesion side) of the disclosure) refers to a material or substance in which less than 30 mg of the material or substance dissolves in 1 L of water at 25° C.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

Chemical Terms

It is to be understood that the terminology employed herein is for the purpose of describing particular embodiments and is not intended to be limiting.

At various places in the present specification, substituents of compounds of the present disclosure are disclosed in groups or in ranges. It is specifically intended that the present disclosure include each and every individual subcombination of the members of such groups and ranges. For example, the term "$C_1$-$C_6$ alkyl" is specifically intended to individually disclose methyl, ethyl, propyl, butyl, pentyl, and hexyl. Furthermore, where a compound includes a plurality of positions at which substitutes are disclosed in groups or in ranges, unless otherwise indicated, the present disclosure is intended to cover individual compounds and groups of compounds (e.g., genera and subgenera) containing each and every individual subcombination of members at each position.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms). In some embodiments, an alkyl group is unbranched (i.e., is linear); in some embodiments, an alkyl group is branched. Alkyl groups are exemplified by methyl, ethyl, n- and iso-propyl, n-, sec-, iso- and tert-butyl, neopentyl, and the like.

As used herein, the term "alkylene" refers to a saturated divalent linker having a specified size (e.g., $C_1$-$C_6$ alkylene). They include straight-chain, branched-chain, and cyclic forms as well as combinations of these, containing only C and H when unsubstituted. Because they are divalent, they can link together two parts of a molecule. Examples are $—CH_2—$, $—CH_2CH_2—$, $—CH_2CH_2CH_2—$, $—CH_2CH_2CH_2CH_2—$, $—CH_2CH_2CH_2CH_2CH_2—$, and $—CH_2CH_2CH_2CH_2CH_2CH_2—$. These groups can be substituted by the groups typically suitable as substituents for alkyl, groups as set forth herein.

As used herein, the terms "C0-C3 alkyl-benzene-diol" and "C0-C3 alkyl-benzene-triol" refer to substituents that optionally include an alkyl chain of 0 to 3 carbons in length that terminate in a benzene-diol or benzene-triol. The substituents can have the formula below:

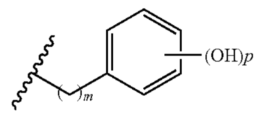

wherein m is 0, 1, 2, or 3; and p is 2 or 3.

Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional. In particular embodiments, a substitution is required by a given structure, and optionally substituted refers to one or more additional substituents. For example, in moiety $-L^2-R^4$ when $L^2$ is an alkyl the moiety describes an alkyl "$L^2$" that is substituted by group $R^4$. In some embodiments, the term optionally substituted X means that X may be optionally substituted with one or more (e.g., 1, 2, 3, 4, 5, or 6) substituents, which may independently be any of the substituents as described herein. Exemplary substituents include, without limitation, alkyl, hydroxyl, alkoxy, aryloxy, halogen, fluoroalkyl, carboxyl, carboxyalkyl, amino, aminoalkyl, monosubstituted amino, disubstituted amino, and quaternary amino groups including from 0 to 6 carbon atoms and from 0 to 4 heteroatoms selected from O, N, F, Cl, Br, and I. Substituents can include methyl, ethyl, carboxymethyl, acyl, $CF_3$, fluoro, and chloro.

DETAILED DESCRIPTION OF THE INVENTION

Figure 1:
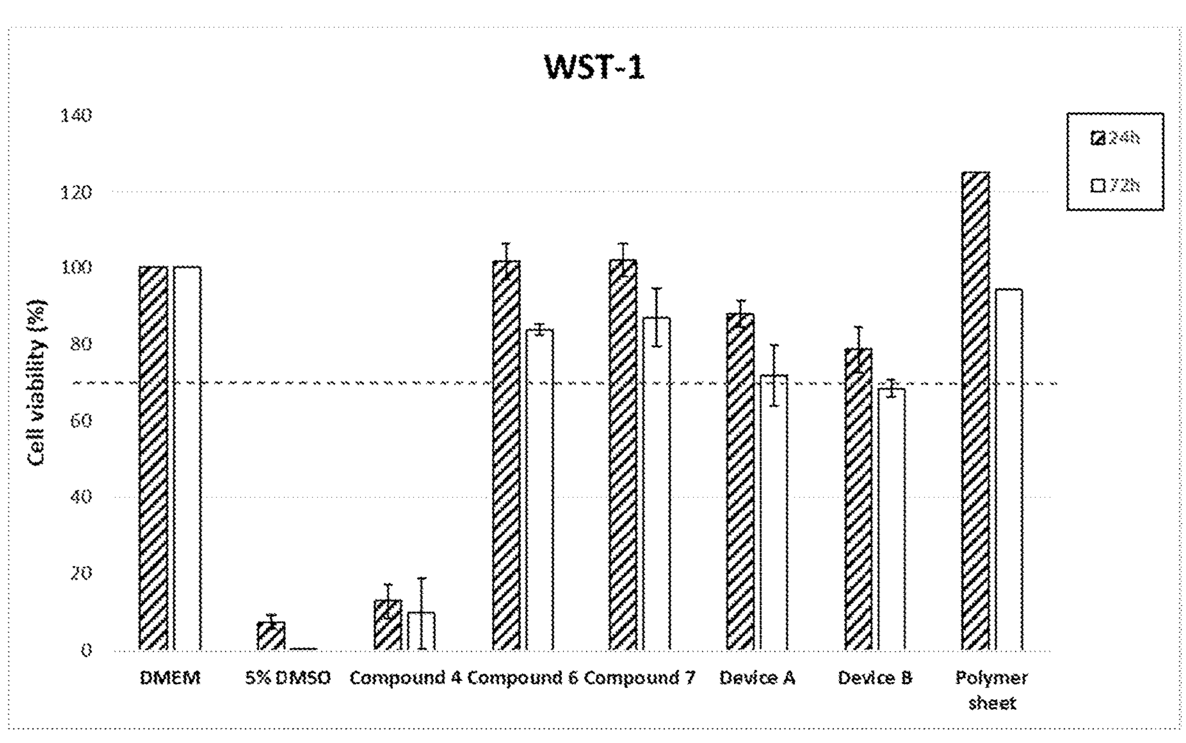
FIG. 1 is a graph showing cytotoxicity of materials in comparison to negative and positive controls (DMEM and 5% DMSO, respectively). Results are expressed as mean±standard deviation; n=4.

The disclosure features adhesive devices for holding objects (e.g., bone fragments) fixed with respect to each other. The disclosed device is useful for attaching to bone or to secure a material to a tissue in order to provide stability or support. The disclosed device may eliminate or reduce the need to use staples, sutures, tacks, screws, or the like to secure or repair damaged tissues (or bone), or to secure implants within the body.

Devices A device of the disclosure can be used to hold two or more objects (e.g., bone fragments, ligaments, tendons) fixed with respect to each other. The device of the disclosure can be made of a gradient of a mixture of one or more adhesives (e.g., polymer(s) having the structure of formula (I) described herein) and one or more fillers (e.g., non-adhesive polymers).

Gradient of Adhesive(s), Filler(s), and Heat Transfer Agent(s)

The device of the disclosure may have varying compositions in different sections of the device. For example, the device can include at least two sections: (i) at least one adhesion section (e.g., a section of the device composed of: 30-100% (w/w) of one or more adhesives (e.g., polymer(s) having the structure of formula (I) as described herein), 0-70% (w/w) of one or more fillers (e.g., non-adhesive polymer(s)), and 0.5-60% (w/w) of one or more of heat transfer agent(s))) which adheres to at least one of the objects (e.g. tissues, such as, e.g., bone fragments, ligaments, tendons, etc.); and (ii) at least one support structure (e.g., a section of the device composed of: 40-100% (w/w) of one or more fillers (e.g., a non-adhesive polymer), and 0-60% (w/w) zero or more adhesives and zero or more heat transfer agents). The support structure may be formed from an anchoring material such as, e.g., polycaprolactone. The adhesion section (e.g., a section of the device composed of a sufficiently high amount of adhesive(s)) may be non-tacky at room temperature, and may be softened upon exposure to energy, such as, e.g., ultrasonic energy, infrared radiation, or radiofrequency (RF)). The softened adhesion section can conform to the shape of the object (e.g., a bone fragment) it contacts. Once the energy exposure is ceased, the adhesion section will cool and rigidify, thus binding the object (e.g., a bone fragment) it contacts. The process may be repeated for the second object (and for the third, fourth, fifth object, or however many objects there are to secure to the preceding objects). This reversible softening feature of the adhesion section is advantageous so as to facilitate ease of handing, placement, workflow and control of device application.

The adhesion section and support structure may be arranged to make sides of the device: an adhesion side (where the adhesion section is a coating of one or more adhesives admixed with one or more fillers) can contact and adhere two or more objects (e.g., bone fragments), and a support side that backs the adhesion side. In this case, energy (e.g., ultrasonic energy, infrared radiation, radiofrequency (RF)) may be delivered to the support side of the device through which heat can transfer to the adhesion side (which contacts the object(s)) without significant deformation of the support structure. This selective softening of the adhesive component relative to the support component is advantageous so as to retain the strength and/or performance of the support structure.

The adhesion section (or adhesion side) may be composed of an admixture of adhesives (e.g, polymer(s) having the structure of formula (I) as described herein) and fillers that may be varied to alter properties of the device of the disclosure such as, e.g., adhesion strength, tackifying temperature, cytotoxicity, tensile strength, time of rigidification, surface fouling resistant properties, brittleness, and viscosity.

The support structure (or support side) may be composed of an admixture of fillers and adhesives that may be varied to alter properties of the support, such as, e.g., porosity (e.g., having pores or texture in which an adhesive may fill), brittleness (e.g., the support structure (or support side) preferably can bend or twist 90° without flaking), flexibility, surface fouling properties, and tensile strength. Additionally, the supporting structure (or support side) may contain a perceptible pattern or texture to aid in determination of direction and orientation for application. This pattern may contain a pattern which provides both a visual and/or tactile perception for determining orientation.

A device (and its components, e.g., the adhesive polymers and non-adhesive polymers that make up the adhesion section (and adhesion side) and support structure (and support side)) of the disclosure may be optionally biodegradable and optionally biocompatible. Furthermore, the device (and its components described herein) may be optionally bioresorbable.

Adhesives of the Disclosure

A device of the disclosure may contain a mixture of one or more adhesives having the structure of formula (I):

formula (I)

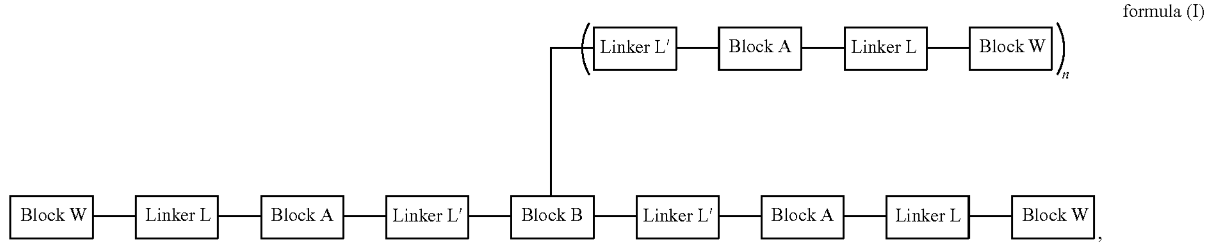

where n is an integer from 0 to 4 (e.g., n=1, 2, 3, or 4);

Block B is an oligomer derived from a polyester, polyether, polalkylene glycol, polysilicone, or polycarbonate with a MW<10,000 g/mol (e.g., 2±1 KDa, 4±2 KDa, 5±2.5 KDa, or 8±2 KDa);

Block A includes an optionally substituted $C_1$-$C_6$ alkylene, wherein Block A is derived from a diisocyanate crosslinker;

Block W includes an optionally substituted $C_0$-$C_3$ alkylbenzene-diol or optionally substituted $C_0$-$C_3$ alkylbenzene-triol;

Linker L' includes a carbamate; and

Linker L includes a urea.

In some embodiments, Block B includes an oligomer derived from a polyester, polalkylene glycol, polysilicone, or polycarbonate. In particular embodiments, the Block B oligomer has a MW≤4,000 g/mol (e.g., 1±0.5 KDa, 2±0.5 KDa, or 3±1 KDa).

Block B can have the structure of formula (II), formula (III), formula (IV), formula (V), or formula (IV):

formula (II)

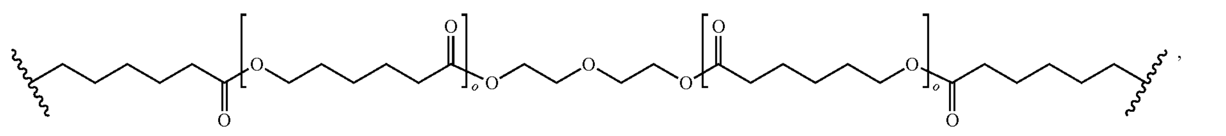

formula (III)

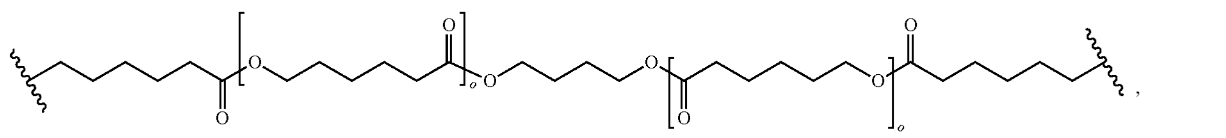

formula (IV)

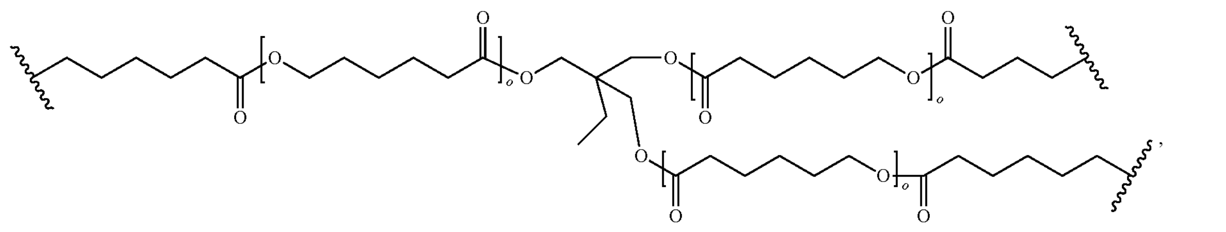

formula (V)

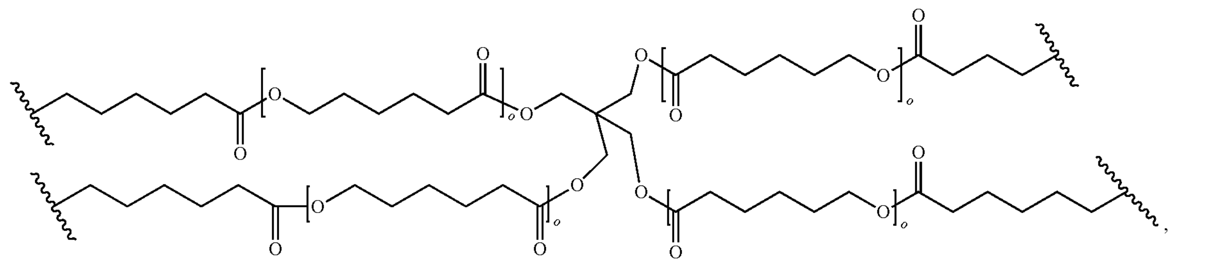

-continued formula (VI)

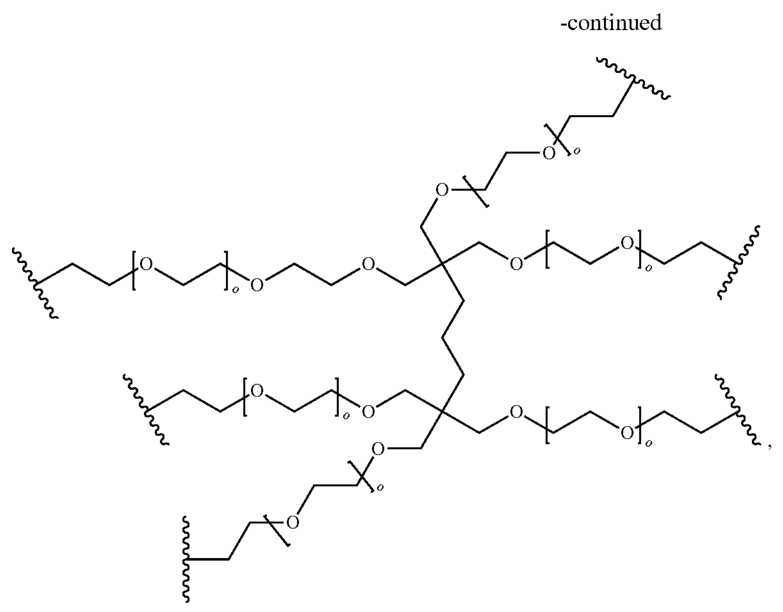

where each o is, independently, an integer from 0 to 20 (e.g., n=0-4, 2-6, 4-10, 5-15, or 10-20).

Block A can have the structure of formula (VII):

formula (VII)

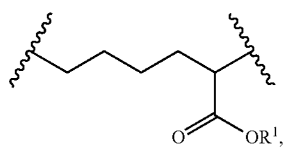

where $R^1$ is $C_1$-$C_3$ alkyl.

Linker L' can have the structure:

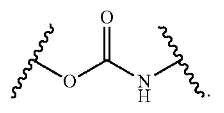 [SMILES: *NC(=O)O*]

Linker L can have the structure:

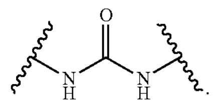 [SMILES: *NC(=O)N*]

Block W can have the structure:

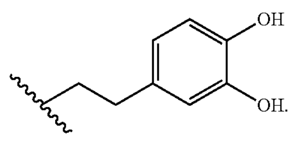 [SMILES: *CCc1ccc(O)c(O)c1]

The isolated adhesive compound can have a tackifying temperature of at least 10° C., at least 15° C., at least 20° C., at least 25° C., or between from 10° C. to 55° C. Blended materials containing an adhesive compound can have a tackifying temperature at least 40° C. (e.g., at least 42° C., at least 45° C., at least 50° C., at least 55° C., or between from 40° C. to 55° C.).

An adhesive or admixture of adhesives of the disclosure may be optionally biodegradable and optionally biocompatible. Furthermore, the adhesive or admixture of adhesives may be optionally bioresorbable. An adhesive or admixture of adhesives of the disclosure can have water solubilities less than 30 mg per L of water.

Generally, adhesives for use in biomedical devices as found in the prior art all teach of the assembly of irreversible crosslinked networks by virtue of large polymeric assemblies either use or are formed chemically from the monomers (e.g. US20140311673A1, WO2017044896A1, WO2014158288A1, US20120029559A1, US20160346424A1, WO2016134304A1, PCT/CA2020051781). They either teach that low molecular weight molecules with low viscosity must be used for flowing before cure or, when large solid polymeric materials are used, solvents or other diluents are necessary to make them flowable. The use of solvents in biomedical adhesives, however, introduces unnecessary toxicity and/or impedes the curing and bonding of the adhesive. Further, flowable systems are susceptible to runoff or leaching of reactive adhesive components and/or oxidants away from the site of application, and/or retention of unreacted species, all of which can present as inflammatory responses in vivo.

Compared to the prior art, the adhesives of formula I are not dependent upon in situ curing reactions for adhesion, and are not susceptible to adhesive leaching/runoff from the application site which can result in undesired side reactions and inflammatory complications. Further, the nature of Block B also means that these adhesives are not particularly prone to swelling and, therefore, inflammatory complications due to the swelling of the device in vivo. The reversible softening properties of the adhesives at temperatures close to physiological temperatures also introduces the benefits of not requiring solvent for surface wetting, of being non-tacky at room temperature, thereby facilitating facile workflow, and of not requiring high temperatures for adhesive softening so as to mitigate the risk of tissue necrosis.

Filler

A device of the disclosure can contain a varying amount (or gradient) of one or more fillers. A filler can be non-adhesive materials or substances that may be added to alter properties of the device of the disclosure such as, e.g., adhesion strength, tackifying temperature, cytotoxicity, tensile strength, time of rigidification, and viscosity. For example, a filler can be, e.g., polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), hydroxyapatite (HA), tetracalcium phosphate (TTCP), tricalcium phosphate (TCP), dicalcium phosphate (DCP), or a copolymer thereof. Preferably, the support structure (or support side) can contain one or more of polycaprolactone (PCL), polydioxanone (PDX), poly(lactic-co-glycolic acid) (PLGA), or poly-3-hydroxybutyrate (P3HB), and a copolymer thereof. More preferably, the support structure will present a melting temperature at least 20° C. higher than that of the adhesive component (e.g., at least 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., or 150° C. higher than that of the adhesive component). Even more preferably, the support structure will present a melting temperature of at least 100° C. higher than the adhesive component.

A filler or admixture of fillers of the disclosure may be optionally biodegradable and optionally biocompatible. Furthermore, the filler or admixture of fillers may be optionally bioresorbable.

Heat Transfer Agent

An adhesion section (or adhesion side) can contain one or more of a heat transfer agent (e.g., a compound that may accelerate the formation of a softened adhesive) in the adhesion section or the adhesion side of the device. The heat transfer agent may be a salt, such as, e.g., sodium chloride, iron(III) phosphate dihydrate, iron(III) citrate monohydrate, hydroxyapatite, tetracalcium phosphate (TTCP), tricalcium phosphate (TCP), dicalcium phosphate (DCP), or sodium carbonate.

Softening and Rigidification of the Device

An adhesion section (or adhesion side) can reversibly soften (e.g., decrease in stiffness) or rigidify (e.g., increase in stiffness) when exposed to energy (e.g., ultrasonic energy, infrared radiation, radiofrequency (RF)) or when cooled (e.g., cooling at ambient temperature without exposure to the energy described herein), respectively. The adhesion section (or adhesion side) is softened if the adhesive or admixture of adhesives has undergone a phase transition from solid to softened state (rigid to malleable state), and can form strings of softened polymer when contacted with a glass pipette tip. Once softened, the adhesion section (or adhesion side) can be contacted with one or more of the objects to be affixed. The softened adhesion section (or adhesion side) can subsequently rigidify within 120 seconds (or less) (e.g, less than 10 seconds) once the adhesion section (or adhesion side) is no longer exposed to energy (e.g., ultrasonic energy, infrared radiation, RF). Preferably, the disclosed adhesion section (or adhesion side) has a tackifying temperature of 40° C. or greater.

Dimensions of the Device

The device of the disclosure may have a thickness between 0.02-1.5 mm (e.g., 0.3±0.2 mm). Depending on the application and mass of the tissue/bone to be stabilized, this thickness will vary accordingly. For example, a thinner device may be used for soft tissue applications (e.g., 0.05 mm thick) whereas a thicker device may be used for bone stabilization (e.g., 1.0 mm thick). Accordingly, the time required to soften the adhesion section (or adhesion side) will be proportional to the thickness of the device. Furthermore, the time required to rigidify will also be proportional to the thickness of the device.

The device of the disclosure may be prepared as a sheet (having all the components of a device described herein (e.g., an adhesion section, a support structure)) up to 100 mm long and 100 mm wide (e.g., 60 mm×60 mm). The sheet can be cut to any dimension and shape (e.g., 10 mm×40 mm) having a thickness as described herein.

Surface Fouling Resistant Properties

The device (specifically, the adhesion section(s) or adhesion side) of the disclosure can resist surface fouling in the presence of aqueous media (e.g., blood). The adhesive or the admixture of adhesives described herein can bind to objects (e.g., tissues that are wet or dry) as described herein. Once bound, the adhesive or the admixture may remain bound to the object(s) in the presence of aqueous media (e.g., blood). For example, a device of the disclosure can bind two (or more) objects in the presence of blood (e.g., horse blood or sheep blood).

Uses and Methods of Treatment

The disclosed device is useful for attaching to objects (e.g., bone), or to secure an object to another object (e.g., a material to a tissue) in order to provide stability or support. The disclosed device may eliminate or reduce the need to use staples, sutures, tacks, screws, or the like to secure or repair damaged tissues (or bone), or to secure implants within the body.

Attaching to Bone

The device of the disclosure may be useful for holding bone fragments (e.g., bone fragments in or from a subject) fixed with respect to each other.

Two or more bone fragments may be adhered (and thus secured) to one or more of the device disclosed herein. A bone fragment may be contacted with an adhesion section (or adhesion side) of the device. Another bone fragment may be in contact with the same adhesion section (or adhesion side), or a second adhesion section of the device. The contacted adhesion section may then be softened using an energy source such as, e.g., ultrasonic energy, infrared radiation, radiofrequency (RF). After cooling, the adhesion section will solidify and bind to the bone fragment. The process may then be repeated for each adhesion section and bone fragment contact area. The bound device can thus stabilize the fracture, and maintain physiological alignment necessary for bone union. The process may also be done in situ or ex situ (e.g., a fragment may be removed from the body, contacted, and bonded with an adhesion section (or adhesion side) of the device, then put back in place and further secured), The device of the disclosure may hold two or more (e.g., 2 to 5, 6 to 10, 11 to 15, 16 to 20, 21 to 25, 26 to 30, 31 to 35, 36 to 40, 41 to 45, 46 to 50 or more) bone fragments fixed with respect to each other. The bone fragments may be fixed with respect to each other with at least one device. In some cases, two or more (e.g., 2 to 5, 6 to 10, 11 to 15, 16 to 20, 21 to 25, 26 to 30, 30 to 40, 40 to 50 or more) of the disclosed device may be used to hold two or more bone fragments fixed with respect to each other.

The device of the disclosure may be used in combination with current standards of care, such as, e.g., stabilizing conventional plates, holding communitions or scaffolds in place in load bearing regions.

Tissue Scaffold

The device of the disclosure can be used to hold a tissue scaffold or filler material in place within a defect in order to allow for regeneration to occur.

Attaching to a Previously Applied Device

The device of the disclosure may be used for attaching to objects (e.g., bone), or to secure an object to another object (e.g., a material to a tissue) by applying an additional device over a previously applied device of the disclosure to increase the rigidity of the fixation.

EXAMPLES

The examples described herein serve to illustrate the present invention, and the invention is not limited to the examples given.

Abbreviations

DSC differential scanning calorimetry
DMAc dimethylacetamide
DMSO dimethylsulfoxide
h hour(s)
LDI Ethyl Ester L-Lysine Diisocyanate
min minute(s)
MW molecular weight
mL milliliter(s)
MS mass spectrometry
m/v mass/volume
NMR nuclear magnetic resonance
PCL polycaprolactone
PDX polydioxanone
TEA triethylamine
TGA thermogravimetric analysis
THF tetrahydrofuran

Example 1. Synthesis of Adhesives

Compound 1

Compound 1 was synthesized via a 3-stage 1-pot method under $N_2$ atmosphere (Scheme 1). The PCL polyol (polycaprolactone diol; MW 1250 g/mol) was dried in a 2-necked round bottom flask for 2 h at 75° C. under vacuum, then dissolved in DMAc solvent (~1:5 m/v ratio) and allowed to cool to room temperature under $N_2$ atmosphere. 2.1 molar equivalents of LDI (Ethyl Ester L-Lysine Diisocyanate) was added, and the reaction stirred at room temperature for 1 h, ramped to 75° C. over 2 h, held at 75° C. for 1 h, and finally stirred at room temperature overnight. Dopamine hydrochloride (2 molar equivalents) was then added into the reaction and stirred until it was fully dissolved. The reaction was placed in an ice bath, and triethylamine (TEA; 2 molar equivalents) was added dropwise. The reaction was allowed to proceed overnight. The reaction was filtered to remove triethylamine hydrochloride by-product, and the resulting filtrate was stirred in a large excess (~10× volume of the reaction) of ether overnight to precipitate the adhesive. The supernatant was decanted and the precipitated adhesive was subsequently redissolved in a minimum volume of hot acetone/ethanol (90:10 v/v) and reprecipitated by solvent exchange centrifugation with ether (x3; 1:9 v/v). Compound 1 was obtained as a white crystalline powder after extended drying under vacuum at room temperature (n is about 5 (average)). 100% dopamine functionalization was observed by $^{1}$H-NMR.

Scheme 1 Synthesis of polycaprolactone diol-derived adhesive, Compound 1.
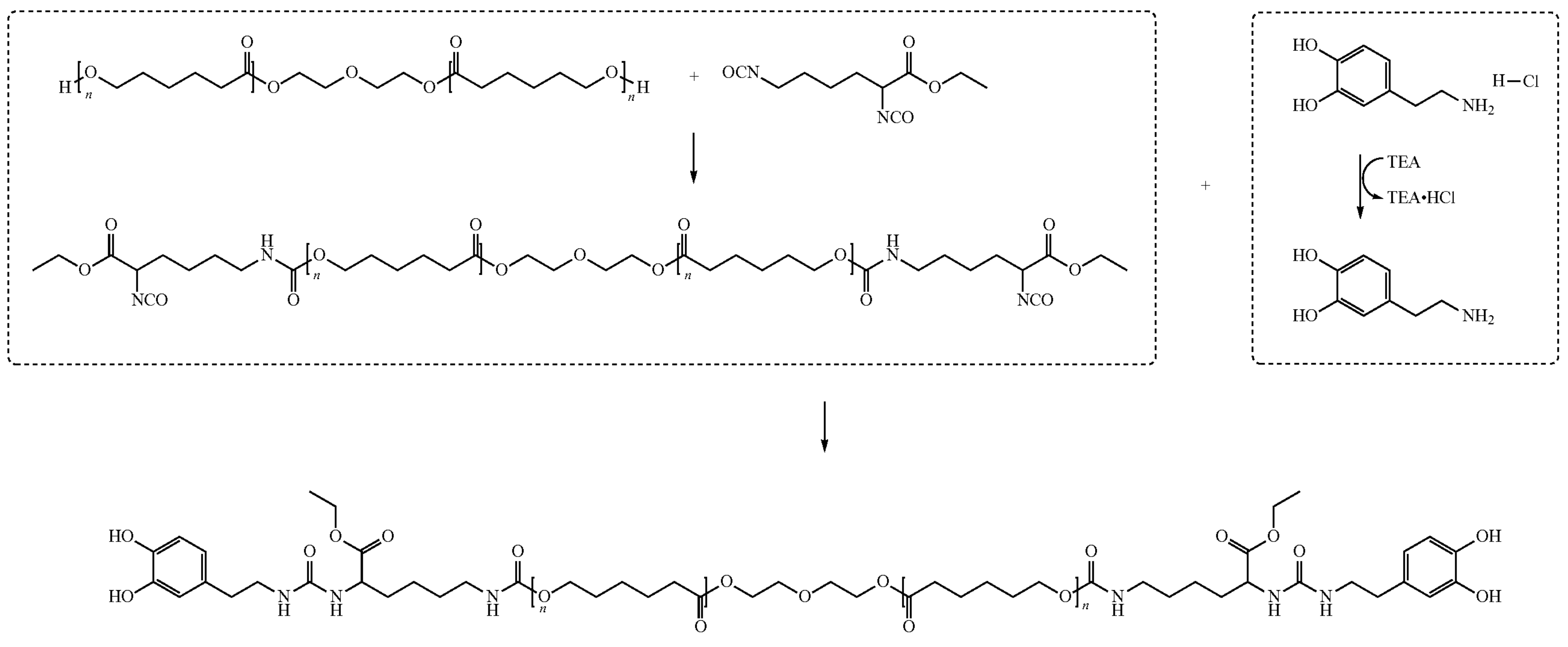

Compound 2

Compound 2 was synthesized via a 3-stage 1-pot method under $N_2$ atmosphere (Scheme 2). The PCL polyol (polycaprolactone diol; MW 2000 g/mol) was dried in a 2-necked round bottom flask for 2 h at 75° C. under vacuum, then dissolved in DMAc solvent (~1:5 m/v ratio) and allowed to cool to room temperature under $N_2$ atmosphere. 2.1 molar equivalents of LDI (Ethyl Ester L-Lysine Diisocyanate) was added, and the reaction was stirred at room temperature for 1 h, ramped to 75° C. over 2 h, held at 75° C. for 1 h, and finally stirred at room temperature overnight. Dopamine hydrochloride (2 molar equivalents) was then added into the reaction and stirred until it was fully dissolved. The reaction was placed in an ice bath, and triethylamine (TEA; 2 molar equivalents) was added dropwise. The reaction was allowed to proceed overnight. Upon completion, the reaction mixture was filtered to remove the triethylamine hydrochloride by-product. The adhesive was then precipitated by solvent exchange centrifugation with ether (x3; 1:9 v/v), then filtered under vacuum. The adhesive was then redissolved in a minimum volume of hot acetone/ethanol (90:10 v/v) and reprecipitated as described above with ether. Compound 2 was obtained as a hard white waxy solid after extended drying under vacuum at room temperature (n is about 8.3 (average)). $^1$H-NMR analysis of Compound 2 demonstrated 73% dopamine functionalization.

Scheme 2 Synthesis of polycaprolactone diol-derived adhesive, Compound 2
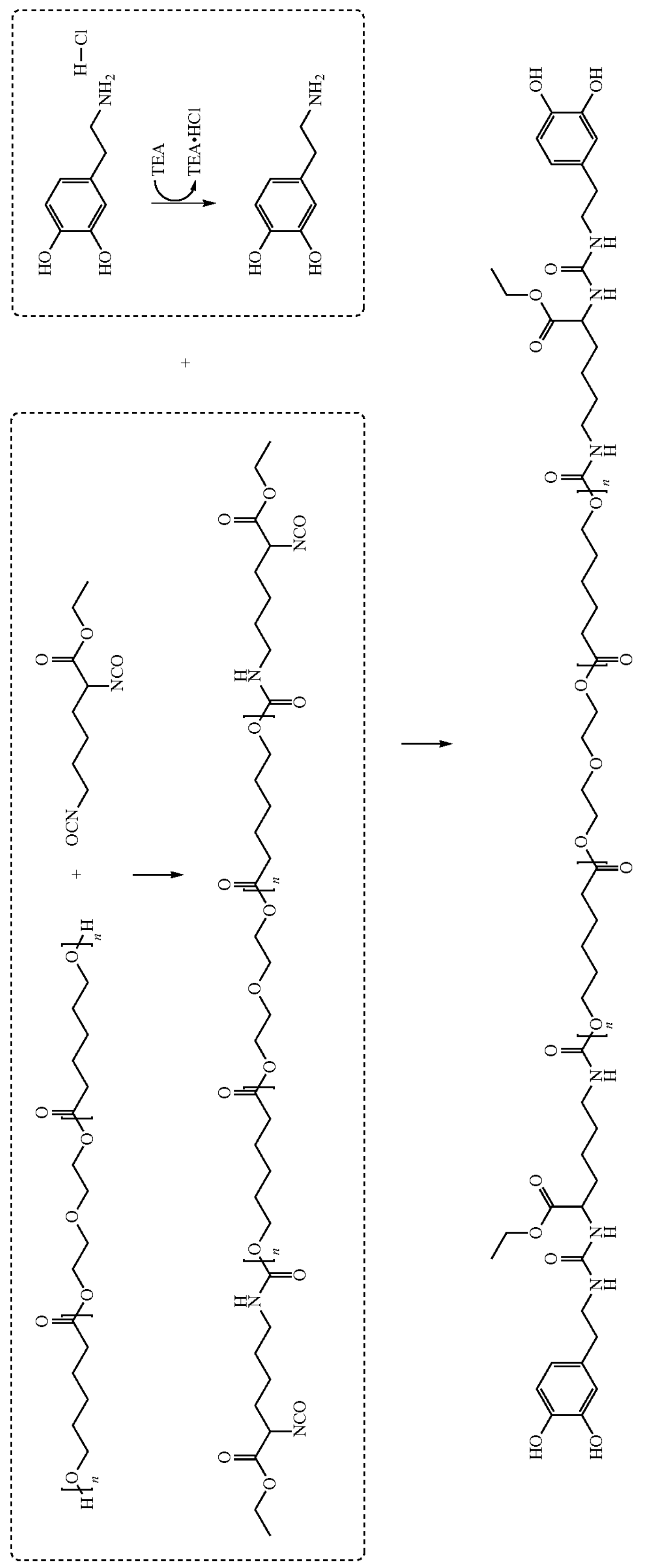

Compound 3

Compound 3 was synthesized via a 3-stage 1-pot method under $N_2$ atmosphere (Scheme 3). The PCL polyol (polycaprolactone diol; MW 4000 g/mol) was dried in a 2-necked round bottom flask for 2 h at 100° C. under vacuum, then dissolved in DMAc solvent (~1:5 m/v ratio) and allowed to cool to room temperature under $N_2$ atmosphere. 2 molar equivalents of LDI (Ethyl Ester L-Lysine Diisocyanate) was added, and the reaction was stirred at room temperature for 1 h, ramped to 75° C. over 2 h, held at 75° C. for 1 h, and finally stirred at room temperature overnight. Dopamine hydrochloride (2 molar equivalents) was then added into the reaction and stirred until it was fully dissolved. The reaction was placed in an ice bath, and triethylamine (TEA; 2 molar equivalents) was added dropwise. The reaction was then removed to room temperature and allowed to proceed overnight. Upon completion, the adhesive was precipitated by stirring in a large excess (~10× volume of reaction) of acidified water. The adhesive was then filtered over vacuum and washed with copious amounts of distilled water until the filtrate was no longer acidic. Compound 3 was obtained as a fluffy white powder after extended freeze drying (n is about 17 (average)). $^{1}H$-NMR analysis of Compound 3 demonstrated 82% dopamine functionalization.

Scheme 3 Synthesis of polycaprolactone diol-derived Compound 3.
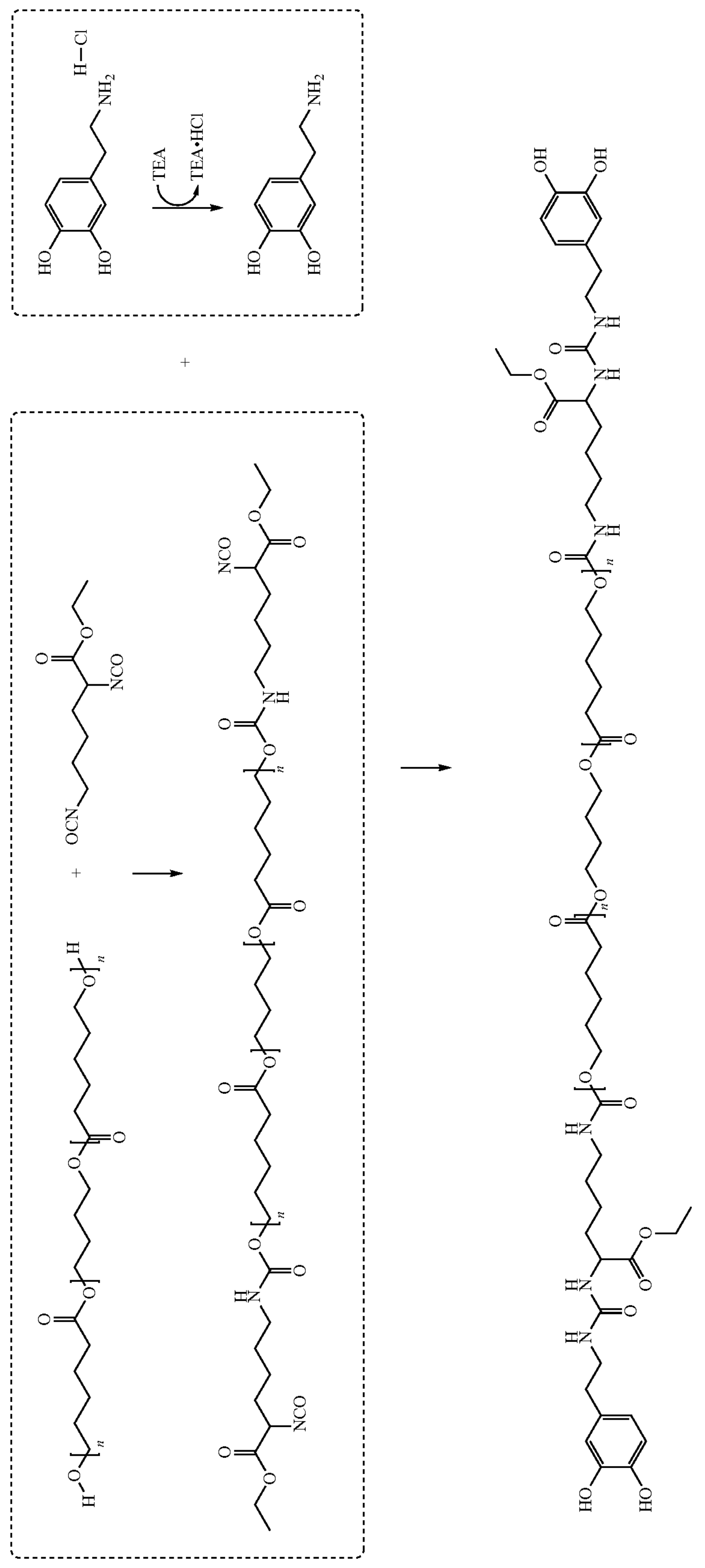

Compound 4

Compound 4 was synthesized via a 3-stage 1-pot method under $N_2$ atmosphere (Scheme 4). The PCL polyol (polycaprolactone triol; MW 300 g/mol) was dried in a 2-necked round bottom flask for 2 h at 75° C. under vacuum, then dissolved in DMAc solvent (~1:5 m/v ratio) and allowed to cool to room temperature under $N_2$ atmosphere. 3 molar equivalents of LDI (Ethyl Ester L-Lysine Diisocyanate) was added, and the reaction stirred at room temperature for 1 h, ramped to 75° C. over 2 h, held at 75° C. for 1 h, and finally stirred at room temperature overnight. Dopamine hydrochloride (3.1 molar equivalents) was then added into the reaction and stirred until it was fully dissolved. The reaction was placed in an ice bath, and triethylamine (TEA; 3 molar equivalents) was added dropwise. The reaction was allowed to proceed overnight. Upon completion, the reaction was filtered to remove the triethylamine hydrochloride residue and the adhesive was precipitated by solvent exchange centrifugation with acidified water (x1; 1:3 v/v). The adhesive was then washed, via solvent exchange centrifugation, with water until neutral (1:4 v/v) and ether (x4; 1:9 v/v). The adhesive was redissolved in a minimum volume of hot acetone/ethanol (90:10 v/v) and was reprecipitated by solvent exchange centrifugation with ether (x3; 1:9 v/v). Compound 4 was finally obtained as a white crystalline powder after extended drying under vacuum at room temperature (n is about 0.5 (average)). $^{1}$H-NMR analysis of Compound 4 demonstrated 80% dopamine functionalization.

Scheme 4 Synthesis of polycaprolactone triol-derived Compound 4.
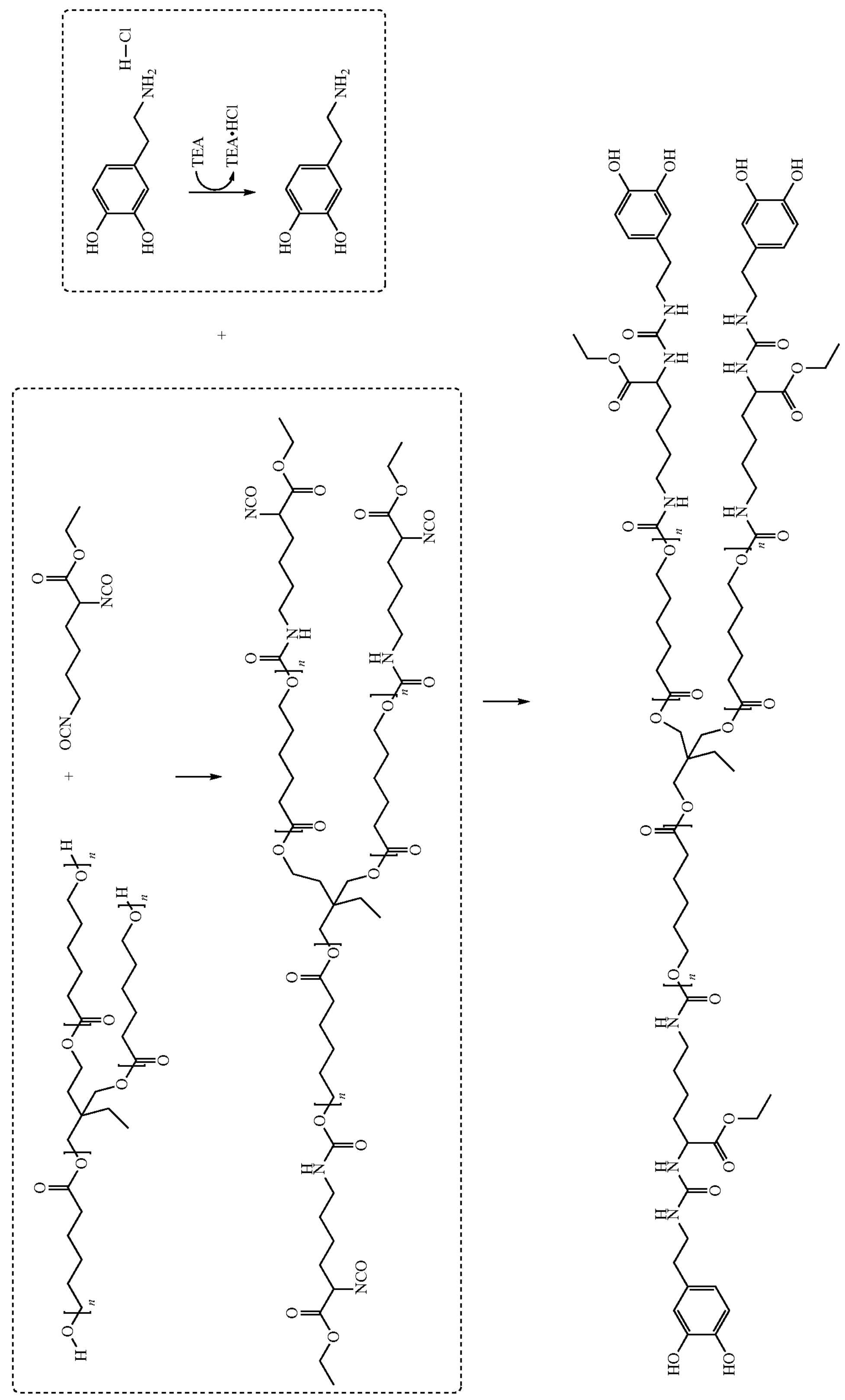

Compound 5

Compound 5 was synthesized via a 3-stage 1-pot method under $N_2$ atmosphere (Scheme 4). The PCL polyol (polycaprolactone triol; MW 900 g/mol) was dried in a 2-necked round bottom flask for 2 h at 75° C. under vacuum, then dissolved in DMAc solvent (~1:5 m/v ratio) and allowed to cool to room temperature under $N_2$ atmosphere. 3.1 molar equivalents of LDI (Ethyl Ester L-Lysine Diisocyanate) was added, and the reaction stirred at room temperature for 1 h, ramped to 75° C. over 2 h, held at 75° C. for 1 h, and finally stirred at room temperature overnight. Dopamine hydrochloride (3 molar equivalents) was then added into the reaction and stirred until it was fully dissolved. The reaction was placed in an ice bath, and triethylamine (TEA; 3 molar equivalents) was added dropwise. The reaction was allowed to proceed overnight. Upon completion, the reaction was filtered to remove the triethylamine hydrochloride residue and the adhesive was precipitated by solvent exchange centrifugation with acidified water (x1; 1:3 v/v). The adhesive was then washed, via solvent exchange centrifugation, with water until neutral (1:4 v/v) and ether (x4; 1:9 v/v). The adhesive was redissolved in a minimum volume of hot acetone/ethanol (90:10 v/v) and was reprecipitated by solvent exchange centrifugation with ether (x3; 1:9 v/v). Compound 5 was finally obtained as a pale yellow hard glassy solid after extended drying under vacuum at room temperature (n is about 2.3 (average)). $^1$H-NMR analysis of Compound 5 demonstrated 77% dopamine functionalization.

Scheme 5 Synthesis of polycaprolactone triol-derived Compound 5.
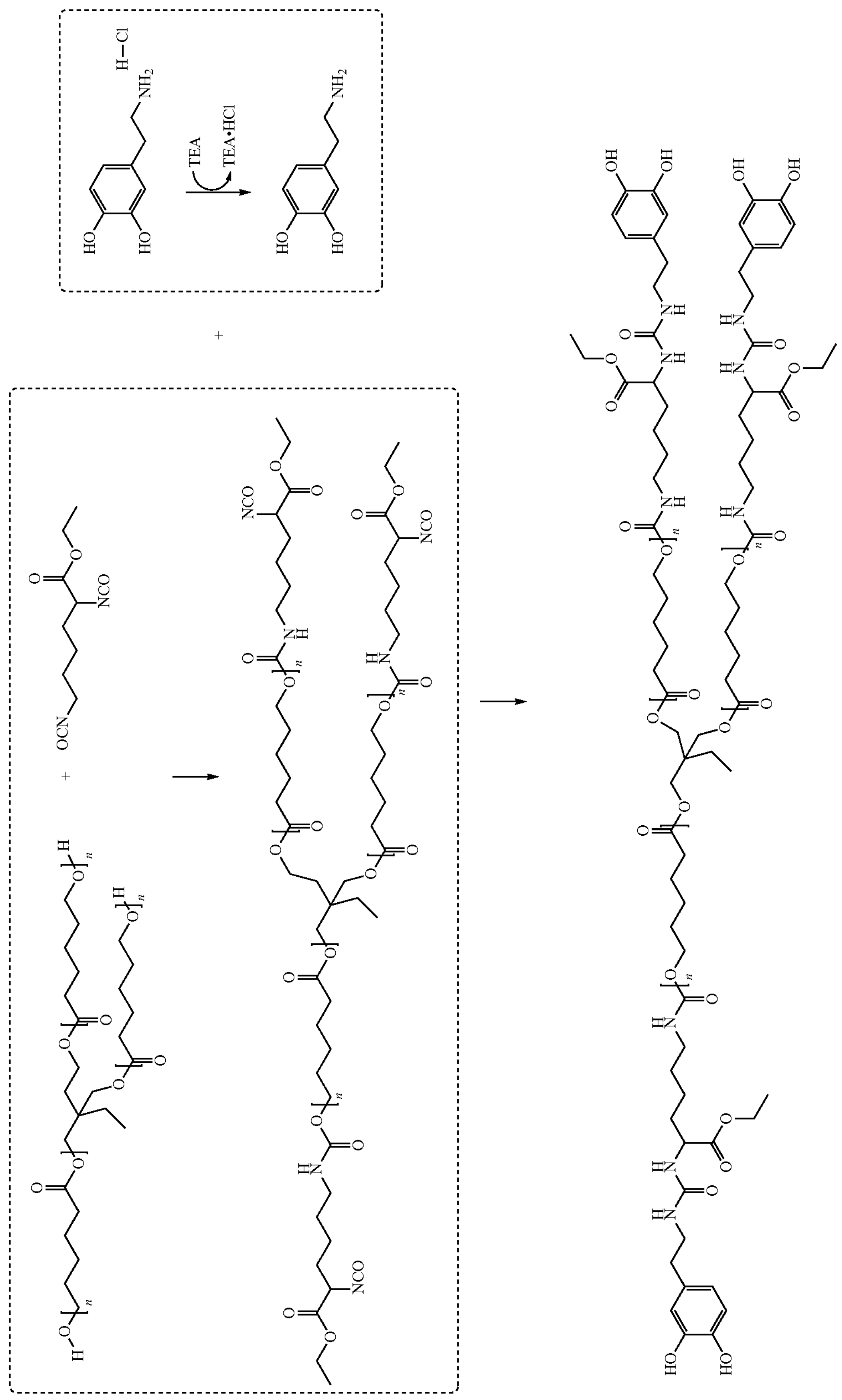

Compound 6

Compound 6 was synthesized via a 3-stage 1-pot method under $N_2$ atmosphere (Scheme 6). The PCL polyol (polycaprolactone triol; MW 2000 g/mol) was dried in a 2-necked round bottom flask for 2 h at 85° C. under vacuum, then dissolved in DMAc solvent (~1:5 m/v ratio) and allowed to cool to room temperature under $N_2$ atmosphere. 3 molar equivalents of LDI (Ethyl Ester L-Lysine Diisocyanate) was added, and the reaction was stirred at room temperature for 1 h, ramped to 75° C. over 2 h, held at 75° C. for 1 h, and finally stirred at room temperature overnight. Dopamine hydrochloride (3.1 molar equivalents) was then added into the reaction and stirred until it was fully dissolved. The reaction was placed in an ice bath, and triethylamine (TEA; 3 molar equivalents) was added dropwise. The reaction was then removed to room temperature and allowed to proceed overnight. Upon completion, the mixture was filtered to remove the triethylamine hydrochloride by-product residue, and the adhesive was precipitated by solvent exchange centrifugation with acidified water (x1; 1:3 v/v). The adhesive was then washed, via solvent exchange centrifugation, with water until neutral (1:4 v/v) and ether (x4; 1:9 v/v). The resulting adhesive was subsequently redissolved in a minimum volume of hot acetone/ethanol (90:10 v/v) and reprecipitated by solvent exchange centrifugation with ether (x4; 1:9 v/v) before being dried for an extended period under vacuum at room temperature to give Compound 6 as a white fluffy powder (n is about 5.5 (average)). $^1$H-NMR analysis demonstrated 90% dopamine functionalization.

Scheme 6 Synthesis of polycaprolactone triol-derived Compound 6.
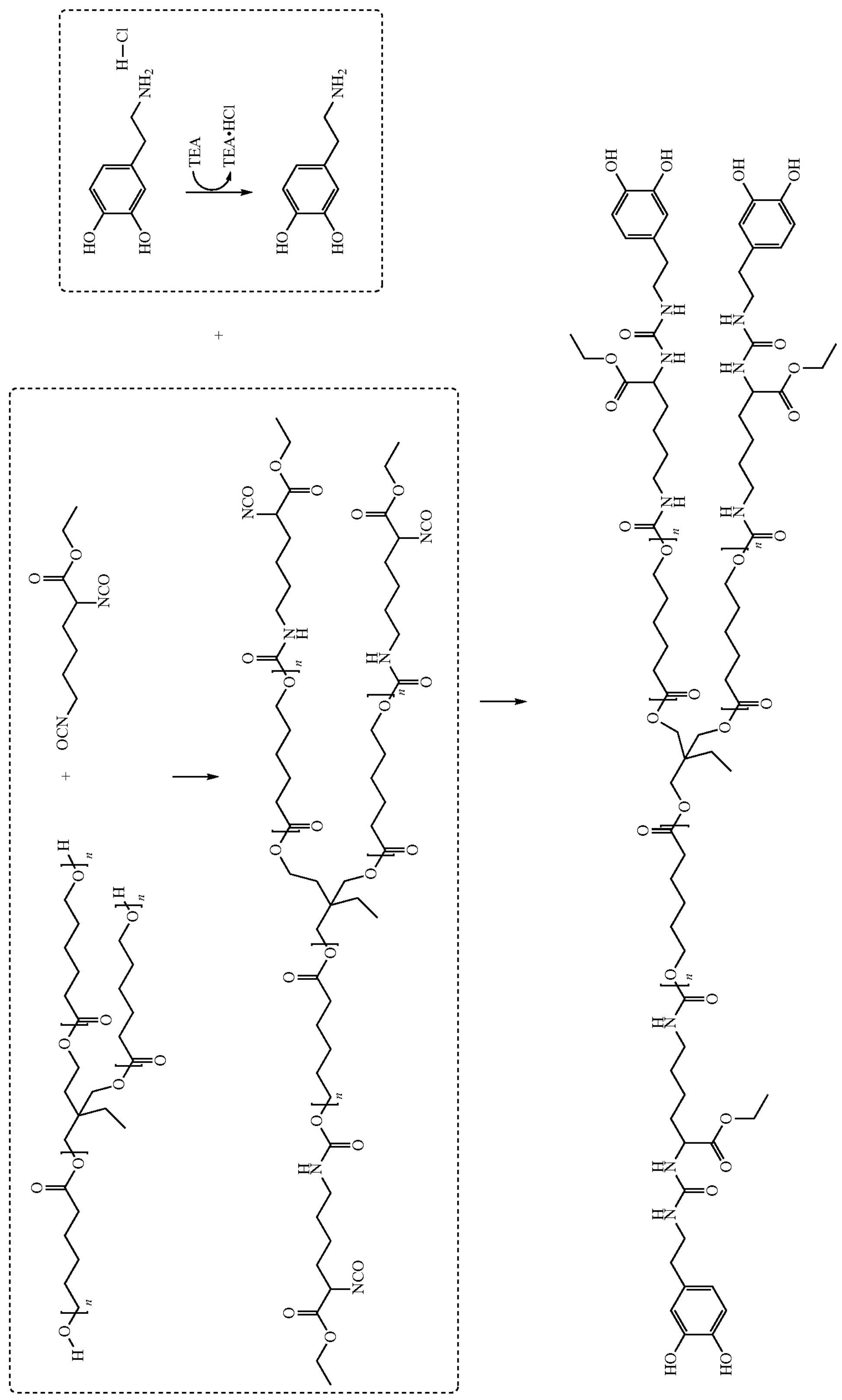

Compound 7

Compound 7 was synthesized via a 3-stage 1-pot method under $N_2$ atmosphere (Scheme 7). The PCL polyol (polycaprolactone tetrol; MW 1000 g/mol) was dried in a 2-necked round bottom for 2 h at 75° C. under vacuum, then dissolved in DMAc solvent (~1:5 m/v ratio) and allowed to cool to room temperature under $N_2$ atmosphere. 4 molar equivalents of LDI (Ethyl Ester L-Lysine Diisocyanate) was added, and the reaction was stirred at room temperature for 1 h, ramped to 75° C. over 2 h, held at 75° C. for 1 h, and finally stirred at room temperature overnight. Dopamine hydrochloride (4.1 molar equivalents) was then added into the reaction and stirred until it was fully dissolved. The reaction was placed in an ice bath, and triethylamine (TEA: 4 molar equivalents) was added dropwise. The reaction was then removed to room temperature and allowed to proceed overnight. Upon completion, the mixture was filtered to remove the triethylamine hydrochloride by-product residue, and the adhesive was precipitated by solvent exchange centrifugation with acidified water (x1; 1:3 v/v). The adhesive was then washed, via solvent exchange centrifugation, with water until neutral (1:4 v/v) and ether (x4; 1:9 v/v). The resulting adhesive was subsequently redissolved in a minimum volume of hot acetone/ethanol (90:10 v/v) and reprecipitated by solvent exchange centrifugation with ether (x4; 1:9 v/v) before being dried for an extended period under vacuum at room temperature to provide Compound 7 as a white spongy solid (n is about 1.9 (average)). $^1$H-NMR analysis demonstrated 89% dopamine functionalization.

Scheme 7 Synthesis of polycaprolactone tetrol-derived Compound 7.
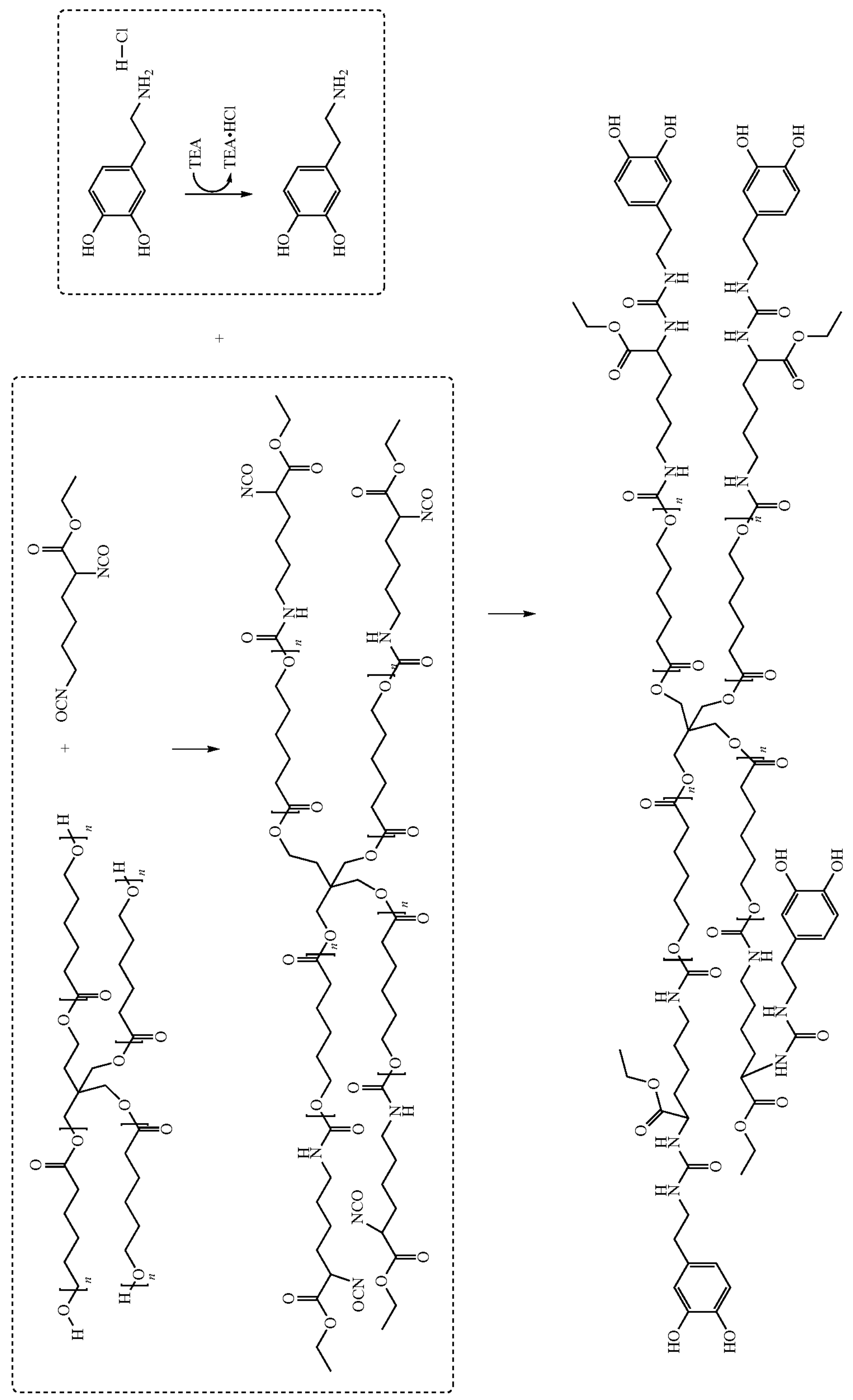

Compound 8

Compound 8 was synthesized via a 3-stage 1-pot method under $N_2$ atmosphere (Scheme 8). The PEE polyol (polyethylether hexol; MW 815 g/mol) was dried in a 2-necked round bottom for 2 h at 75° C. under vacuum, then dissolved in DMAc solvent (~1:5 m/v ratio) and allowed to cool to room temperature under $N_2$ atmosphere. 6 molar equivalents of LDI (Ethyl Ester L-Lysine Diisocyanate) was added, and the reaction was stirred at room temperature for 1 h, ramped to 75° C. over 2 h, held at 75° C. for 1 h, and finally stirred at room temperature overnight. Dopamine hydrochloride (6.1 molar equivalents) was then added into the reaction and stirred until it was fully dissolved. The reaction was placed in an ice bath, and triethylamine (TEA: 6 molar equivalents) was added dropwise. The reaction was then removed to room temperature and allowed to proceed overnight. Upon completion, the mixture was filtered to remove the triethylamine hydrochloride by-product residue, and the adhesive was precipitated by solvent exchange centrifugation with acidified water (x1; 1:3 v/v). The adhesive was then washed, via solvent exchange centrifugation, with water until neutral (1:4 v/v) and ether (x4; 1:9 v/v). The resulting adhesive was subsequently redissolved in a minimum volume of hot acetone/ethanol (90:10 v/v) and reprecipitated by solvent exchange centrifugation with ether (x4; 1:9 v/v) before being dried for an extended period under vacuum at room temperature to provide Compound 8 as pale yellow hard glassy solid. $^{1}$H-NMR analysis demonstrated 78% dopamine functionalization.

Scheme 8 Synthesis of polyethylether hexol-derived Compound 8.
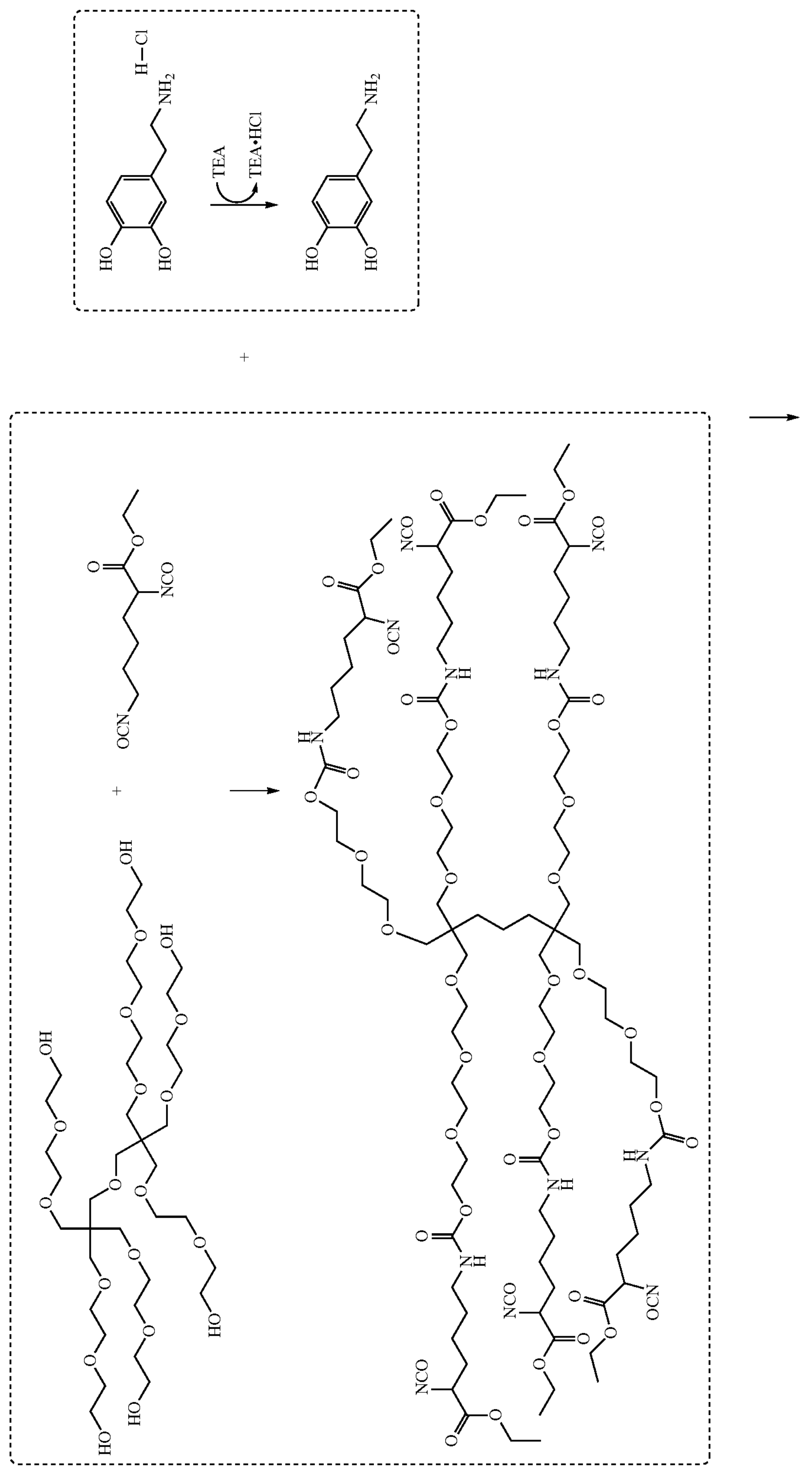

-continued
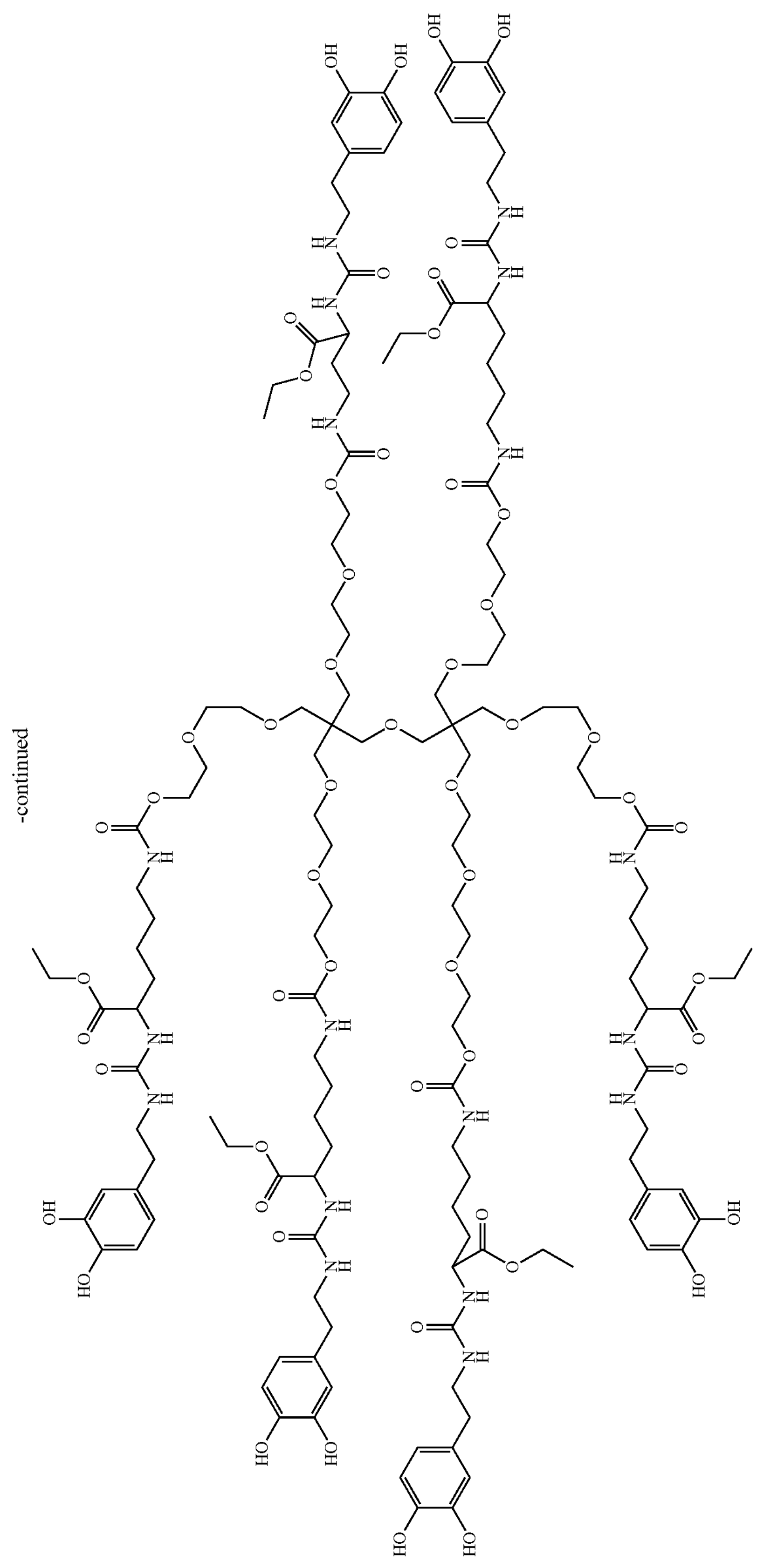

Example 2. Adhesive Blending

Adhesive blends were prepared using either a cryogenic milling process, or a micro-compounding procedure based on the quantity of blended product required. Adhesive blends comprised the adhesives described herein, polymers such as, e.g., PCL (MW=50 kDa, Polysciences, USA), and soluble or insoluble particulates such as, e.g., sodium chloride (Bioshop, USA), hydroxyapatite (Sigma, USA; SS-nano, USA), tetracalcium phosphate (TCP) (Himed, USA) or sodium carbonate (Bioshop USA).

For the cryogenic milling of the adhesive blends, 1-3 g of total mass of adhesive components was added into a steel cannister containing 4 hardened ball bearings. Milling was performed at 30 Hz, and −196° C. on a Retsch Cryomill (Retsch, DE) with a liquid nitrogen attachment, using three, five-minute milling cycles with auto precool and 5 min cooling between cycles. Blends were warmed to room temperature inside the cannister before being transferred to a glass scintillation vial.

Alternately, compounded adhesive filaments were prepared using a 10 mL Xplore Twin Screw Micro-compounder at ~105° C. for approximately 2 min at 200 rpm. The blended adhesives were extruded into filaments and pelleted.

Regardless of blending method, all adhesive blends were dried under vacuum for >2 h at room temperature before being sealed and stored at −20° C. prior to use. Table 1a shows adhesive blends of the disclosure.

TABLE 1a

| Adhesive Blends | | | | |
|---|---|---|---|---|
| | Composition (wt %) | | | |
| Name | Adhesive 1 | Adhesive 2 | Polymer filler | Additive* |
| Blend 1a | Compound 6, 12.5% | Compound 7, 37.5% | Polycaprolactone ($PCL_{50}$; 50 kDa); 50% | — |
| Blend 2a | Compound 4, 12.5% | Compound 7, 37.5% | Polycaprolactone ($PCL_{50}$; 50 kDa); 50% | — |
| Blend 2b | Compound 4, 12.5% | Compound 7, 37.5% | Purasorb PLC7015; 70/30 L-lactide/ Caprolactone copolymer (PLC9517), 50% | — |
| Blend 2c | Compound 4, 12.5% | Compound 7, 37.5% | Poly(L-lactide-co-glycolide); (82:18 lactide:glycolide) (LG824s); 50% | — |
| Blend 2d | Compound 4, 12.5% | Compound 7, 37.5% | Poly(L-lactide) (LG210); 50% | — |
| Blend 2e | Compound 4, 12.5% | Compound 7, 37.5% | Polycaprolactone ($PCL_{14}$; 14 kDa); 50% | — |
| Blend 2f | Compound 4, 12.5% | Compound 7, 37.5% | Compound 3, 50% | — |
| Blend 2g | Compound 4, 12.5% | Compound 7, 37.5% | Pluronic acid (PF127); 50% | — |
| Blend 2h | Compound 4, 12.5% | Compound 7, 37.5% | Hydroxyapatite (HA); 50% | — |
| Blend 2i | Compound 4, 12.5% | Compound 7, 37.5% | Poly(1,4-butylene adipate) (PBA; 12 kDa); 50% | |
| Blend 3a | Compound 4, 25% | Compound 6, 75% | — | — |
| Blend 3b | Compound 4, 45% | Compound 6, 55% | — | — |
| Blend 3c | Compound 4, 48% | Compound 6, 52% | — | — |
| Blend 3d | Compound 4, 50% | Compound 6, 50% | — | — |
| Blend 3e | Compound 4, 55% | Compound 6, 45% | — | — |
| Blend 3f | Compound 4, 75% | Compound 6, 25% | — | — |
| Blend 4a | Compound 4, 25% | Compound 7, 75% | — | — |
| Blend 4b | Compound 4, 50% | Compound 7, 50% | — | — |
| Blend 4c | Compound 4, 75% | Compound 7, 25% | — | — |
| Blend 5a | Compound 6, 25% | Compound 7, 75% | — | — |
| Blend 5b | Compound 6, 50% | Compound 7, 50% | — | — |
| Blend 5c | Compound 6, 75% | Compound 7, 25% | — | — |
| Blend 6a | Compound 4, 12.5% | Compound 7, 37.5% | Polycaprolactone ($PCL_{50}$; 50 kDa); 50% | NaCl, 1.25% |
| Blend 6b | Compound 4, 12.5% | Compound 7, 37.5% | Polycaprolactone ($PCL_{50}$; 50 kDa); 50% | $Na_2CO_3$, 2.5% |
| Blend 6c | Compound 4, 12.5% | Compound 7, 37.5% | Polycaprolactone ($PCL_{50}$; 50 kDa); 50% | NaCl, 2.5% |
| Blend 6d | Compound 4, 12.5% | Compound 7, 37.5% | Polycaprolactone ($PCL_{50}$; 50 kDa); 50% | $SiO_2$, 2.5% |
| Blend 6e | Compound 4, 12.5% | Compound 7, 37.5% | Polycaprolactone ($PCL_{50}$; 50 kDa); 50% | NaCl, 5% |
| Blend 6f | Compound 4, 12.5% | Compound 7, 37.5% | Polycaprolactone ($PCL_{50}$; 50 kDa); 50% | HA (pH 11), 5% |
| Blend 6g | Compound 4, 12.5% | Compound 7, 37.5% | Polycaprolactone ($PCL_{50}$; 50 kDa); 50% | NaCl, 10% |
| Blend 6h | Compound 4, 12.5% | Compound 7, 37.5% | Polycaprolactone ($PCL_{50}$; 50 kDa); 50% | HA (pH 11), 20% |
| Blend 6i | Compound 4, 12.5% | Compound 7, 37.5% | Polycaprolactone ($PCL_{50}$; 50 kDa); 50% | HA (pH 11), 30% |
| Blend 6j | Compound 4, 12.5% | Compound 7, 37.5% | Polycaprolactone ($PCL_{50}$; 50 kDa); 50% | HA (pH 11), 40% |

TABLE 1a-continued

| Adhesive Blends | | | | |
|---|---|---|---|---|
| | Composition (wt %) | | | |
| Name | Adhesive 1 | Adhesive 2 | Polymer filler | Additive* |
| Blend 6k | Compound 4, 12.5% | Compound 7, 37.5% | Polycaprolactone ($PCL_{50}$; 50 kDa); 50% | HA (pH 11), 60% |
| Blend 6l | Compound 4, 12.5% | Compound 7, 37.5% | Polycaprolactone ($PCL_{50}$; 50 kDa); 50% | HA (pH 11), 100% |
| Blend 6m | Compound 4, 12.5% | Compound 7, 37.5% | Poly(1,4-butylene adipate) (PBA; 12 kDa); 50% | HA (pH 11), 60% |
| Blend 6n | Compound 4, 12.5% | Compound 7, 37.5% | Poly(ethylene succinate) (PES; 12 kDa); 50% | HA (pH 11), 60% |
| Blend 6o | Compound 4, 12.5% | Compound 7, 37.5% | Poly(ethylene adipate) (PEA; 10 kDa); 50% | HA (pH 11), 60% |
| Blend 6p | Compound 4, 12.5% | Compound 7, 37.5% | Polycaprolactone ($PCL_{50}$; 50 kDa); 50% | Tetracalcium phosphate (TTCP), 60% |
| Blend 7a | Compound 4, 37.5% | Compound 6, 12.5% | Polycaprolactone ($PCL_{50}$; 50 kDa); 50% | — |
| Blend 7b | Compound 4, 25% | Compound 6, 25% | Polycaprolactone ($PCL_{50}$; 50 kDa); 50% | — |
| Blend 7c | Compound 4, 12.5% | Compound 6, 37.5% | Polycaprolactone ($PCL_{50}$; 50 kDa); 50% | — |
| Blend 8a | Compound 6, 37.5% | Compound 7, 12.5% | Polycaprolactone ($PCL_{50}$; 50 kDa); 50% | — |
| Blend 8c | Compound 6, 12.5% | Compound 7, 37.5% | Polycaprolactone ($PCL_{50}$; 50 kDa); 50% | — |
| Blend 8b | Compound 6, 25% | Compound 7, 25% | Polycaprolactone ($PCL_{50}$; 50 kDa); 50% | — |
| Blend 9a | Compound 3, 50% | Compound 7, 50% | | |
| Blend 9b | Compound 3, 25% | Compound 7, 25% | Polycaprolactone ($PCL_{50}$; 50 kDa); 50% | HA (pH 11), 80% |
| Blend 9c | Compound 3, 25% | Compound 7, 25% | Polycaprolactone ($PCL_{50}$; 50 kDa); 50% | HA (pH 7), 80% |
| Blend 9d | Compound 3, 25% | Compound 7, 25% | Polycaprolactone ($PCL_{50}$; 50 kDa); 50% | HA (pH 5), 80% |
| Blend 9e | Compound 3, 25% | Compound 7, 25% | Polycaprolactone ($PCL_{50}$; 50 kDa); 50% | Tetracalcium phosphate (TTCP), 80% |
| Blend 9f | Compound 3, 25% | Compound 7, 25% | Polycaprolactone ($PCL_{50}$; 50 kDa); 50% | Dicalcium phosphate (DCP), 80% |
| Blend 9g | Compound 3, 25% | Compound 7, 25% | Polycaprolactone ($PCL_{50}$; 50 kDa); 50% | HA (pH 11), 80% |
| Blend 9h | Compound 3, 25% | Compound 7, 25% | Polycaprolactone ($PCL_{50}$; 50 kDa); 50% | HA (pH 7), 80% |
| Blend 9i | Compound 3, 25% | Compound 7, 25% | Polycaprolactone ($PCL_{50}$; 50 kDa); 50% | HA (pH 7), 80% |

*additive weight % is listed as the weight percent of the total organic content; i.e., of Adhesive 1 + Adhesive 2 + Polymer filler.

Example 3. Support Side Preparation

Filaments of polymer blends were created using a micro-compounding procedure. Briefly, polymers were dried under vacuum at room temperature overnight prior to use. For films composed of blends of polymers, the polymers were first compounded into filaments using a 10 mL Xplore Twin Screw Micro-compounder at a temperature suitable to melt the polymer (115-220° C. based on the polymers being compounded) for approximately 5 min at 200 rpm. Polymers were extruded into filaments and pelleted.

Pellets were dried under vacuum and then compression molded into thin films on a Carver Automated heated press at 1000-2000 kg. Briefly, platens were heated to a suitable melting temperature. Filaments are cut into ~3 cm lengths to a specific mass, depending on the size of sheet to be pressed. Teflon liners and molds were used to prevent the polymer melt from sticking to the steel platens. In select cases, teflon liners were textured in order to impart a texture in the resulting sheet (see Example 4). Teflon molds range in thickness from 0.1-0.5 mm. Molding was done by layering steel sheet, Teflon liner, Teflon mold and polymer material, Teflon liner, and steel sheet. The lamellar molding sandwich was placed on the bottom platen and raised to ~1 mm below the top platen. The polymer was melted without any applied force for 10 minutes. After melting, force was increased to ~100-300 kg manually. Once the force dropped to ~0-100 kg, hydraulic pressure was released to allow any air bubbles to dissipate. Force was then increased in auto mode at 15% speed to 1000-2000 kg (depending on desired thickness) for 5 minutes. The lamellar mold set up was transferred to a 37° C. and allowed to cool naturally before removing the sheet from the mold. The sheet was trimmed to remove excess material and stored in a desiccator prior to use. Table 1b shows polymers of the disclosure that make up the support side.

TABLE 1b

| Polymeric Supports | | | | |
|---|---|---|---|---|
| | Composition (wt %) | | Compounding temperature | Platen temperature |
| Name | Polymer component 1 | Polymer component 2 | (° C.) | (° C.) |
| Polymer 1 | Polycaprolactone (PCL; 50 kDa); 100% | — | — | 115 |
| Polymer 2 | Polydioxanone (PDX); 100% | — | — | 130 |
| Polymer Blend 3 | Polydioxanone (PDX); 60% | Polycaprolactone (PCL; 50 kDa); 40% | 115 | 130 |
| Polymer Blend 4 | Polydioxanone (PDX); 80% | Polycaprolactone (PCL; 50 kDa); 20% | 115 | 130 |
| Polymer 5 | Poly(L-lactide-co-glycolide); (82:18 lactide:glycolide) (LG824s), 100% | — | — | 170 |
| Polymer Blend 6 | Poly(L-lactide-co-glycolide); (82:18 lactide:glycolide) (LG824s), 60% | Purasorb PLC7015; 70/30 L-lactide/Caprolactone copolymer (PLC7015), 40% | 185 | 170 |
| Polymer 7 | Purasorb PLC9517; 95/5 L-lactide/Caprolactone copolymer (PLC9517), 100% | — | — | 170 |
| Polymer 8 | Purasorb PLC8516; 85/15 L-lactide/Caprolactone copolymer (PLC8516), 100% | — | — | 170 |
| Polymer Blend 9 | Poly(L-lactide) (LG210), 60% | Purasorb PC17; polycaprolactone (PC17), 40% | 220 | 220 |
| Polymer Blend 10 | Poly(L-lactide-co-glycolide); (82:18 lactide:glycolide) (LG824s), 60% | Polycaprolactone (PCL; 50 kDa); 40% | 185 | 170 |
| Polymer Blend 11 | Purasorb PLC9517; 95/5 L-lactide/Caprolactone copolymer (PLC9517), 30% | Polycaprolactone (PCL; 50 kDa); 70% | 185 | 170 |
| Polymer Blend 12 | Purasorb PLC8516; 85/15 L-lactide/Caprolactone copolymer (PLC8516), 40% | Polycaprolactone (PCL; 50 kDa); 60% | 185 | 170 |
| Polymer Blend 13 | Poly(L-lactide-co-glycolide); (82:18 lactide:glycolide) (LG824s), 50% | Purasorb PLC7015; 70/30 L-lactide/Caprolactone copolymer (PLC7015), 50% | 185 | 170 |

Example 4. Texturing Polymer Sheets

In order to create a texture on the adhesion side of the polymer sheets, subtractive, laser etching was used to texture a Teflon liner, as to impart a positive feature in the polymer sheet during compression molding. Textures were created using computer aided design in Autocad. Textures were laser etched into Teflon sheets on a 60 W $CO_2$ laser engraver (Universal Laser Systems, VLS3.5). After etching, textured Teflon sheets were cleaned with isopropanol and compressed air to remove excess material. One polymer sheet was pressed onto the newly etched Teflon liner and removed in order to further clean the textured liner prior to use. Feature dimensions were tuned using more passes or higher power as necessary, but generally measured 100-200 μm in depth. Textured sheets were then used as liners during compression molding of polymer sheets to induce positive features approximately 100-150 μm in height.

Example 5. Device Assembly

Method 1: Pressed

Cryomilled/compounded adhesive, adhesive blends or adhesive admixtures were hot-pressed onto polymer sheets/films. Briefly, polymer sheets/films (prepared as reported in Example 4) were plasma treated under a partial oxygen atmosphere for at least 2 minutes using a benchtop plasma cleaner (Harrick Plasma, USA). Meanwhile the hot press (Carver, USA) was heated to 75° C. (upper platen) and 70° C. (lower platen). Approximately 0.8 g of adhesive, adhesive blends or adhesive admixtures was placed on to the center of the polymer sheet. The sheet was then placed into a similar laminar mold set up as used for compression molding of the sheet with the adhesion side facing up. The mold thickness was set in order to set the adhesive thickness. The mold was placed on the platen and raised such that the upper platen was <1 mm from the mold. The material was allowed to melt for 5-10 min under no pressure. After the melt step, 800 kg of force was automatically applied at 15% speed and held for an additional 5 min. The mold was removed and allowed to cool to room temperature before removing the resulting polymer sheet/adhesive composite.

Method 2: Laminated

The laminated method comprised lamination of pre-pressed sheets of the support polymer and the adhesive layers onto each other. Adhesive sheets were prepared using a modified version of the compression molding method used for the support side polymers (Example 4). In brief, compounded rods of the adhesive blends were cut lengthwise into 5 mm pieces and approximately 0.8-1.0 g were placed into the compression molding set up. This mold was then placed into the hot press, which was maintained at 105° C. for both platens, so that the compression mold was <1 mm from the top platen to maximize heating. The adhesive was allowed to melt for 5 min and then 1000-4000 kg (depending on desired thickness) of force was applied for 2 min. The mold was then removed from the hot press and cooled to room temperature and the adhesive layer was removed for lamination. Separately, polymer sheets/films (prepared as reported in Example 4) were plasma treated under a partial oxygen atmosphere for at least 2 minutes using a benchtop plasma cleaner (Harrick Plasma, USA). For lamination, the backing layer was placed on top of the adhesive layer between two sheets of Teflon, and then placed into a laminator set to approximately 150-250 F (depending on the adhesive thickness). The resulting sheet was allowed to cool to room temperature before the laminated tape was removed from the Teflon sheets.

TABLE 1c

Devices Formed from Adhesive Blends and Polymeric Supports

| Bone Tape Name | Adhesive composition | Support side composition |
|---|---|---|
| Device A | Blend 1a | Polymer 4 |
| Device B | Blend 2a | Polymer 4 |
| Device C-1 | Blend 4a | Polymer 3 |
| Device C-2 | Blend 2a | Polymer 3 |
| Device C-3 | Blend 2b | Polymer 3 |
| Device C-4 | Blend 2c | Polymer 3 |
| Device C-5 | Blend 2d | Polymer 3 |
| Device C-6 | Blend 2e | Polymer 3 |
| Device C-7 | Blend 2f | Polymer 3 |
| Device C-8 | Blend 2g | Polymer 3 |
| Device C-9 | Blend 2h | Polymer 3 |
| Device C-10 | Blend 2i | Polymer 3 |
| Device D-1 | Blend 4a | Polymer 3 |
| Device D-2 | Blend 6a | Polymer 3 |
| Device D-3 | Blend 6b | Polymer 3 |
| Device D-4 | Blend 6c | Polymer 3 |
| Device D-5 | Blend 6d | Polymer 3 |
| Device D-6 | Blend 6e | Polymer 3 |
| Device D-7 | Blend 6f | Polymer 3 |
| Device D-8 | Blend 6g | Polymer 3 |
| Device D-9 | Blend 6h | Polymer 3 |
| Device D-10 | Blend 6i | Polymer 3 |
| Device D-11 | Blend 6j | Polymer 3 |
| Device D-12 | Blend 6k | Polymer 3 |
| Device D-13 | Blend 6l | Polymer 3 |
| Device D-14 | Blend 6m | Polymer 3 |
| Device D-15 | Blend 6n | Polymer 3 |
| Device D-16 | Blend 6o | Polymer 3 |
| Device D-17 | Blend 6p | Polymer 3 |
| Device E-1 | Blend 6f | Polymer 1 |
| Device E-2 | Blend 6f | Polymer 2 |
| Device E-3 | Blend 6f | Polymer 3 |
| Device E-4 | Blend 6f | Polymer 4 |
| Device E-5 | Blend 6f | Polymer 5 |
| Device E-6 | Blend 6f | Polymer 6 |
| Device E-7 | Blend 6f | Polymer 7 |
| Device E-8 | Blend 6f | Polymer 8 |
| Device F-1 | Blend 9b | Polymer 6 |
| Device F-2 | Blend 9c | Polymer 6 |
| Device F-3 | Blend 9d | Polymer 6 |
| Device F-4 | Blend 9e | Polymer 6 |
| Device F-5 | Blend 9f | Polymer 6 |
| Device F-6 | Blend 9g | Polymer 6 |
| Device F-7 | Blend 9h | Polymer 6 |
| Device F-8 | Blend 9i | Polymer 6 |
| Device F-9 | Blend 9c | Polymer 5 |

Example 6. Analysis of Thermal Stability and Volatiles Content of Adhesive Compounds The volatiles content of adhesive compounds were obtained from simulated TGA experiments. 100 mg of each adhesive compound was massed in heat resistant glass vials at room temperature. Samples were heated to 160° C. under vacuum condition for 1 hour. After 1 hours, sample were left to cool down under vacuum for another hour. The mass of the samples was recorded after they cooled down. Residual solvent was calculated from the percentage of mass loss obtained at 160° C. 2 samples have been tested for each adhesive.

The results are provided in Table 1 d. Table 1 d shows the thermal stability/volatile content of the adhesives obtained under simulated thermogravimetric analyses (sTGA), obtained as the material mass loss up to a pre-determined temperature—the boiling point of the highest boiling solvent (160° C. for DMAc, in our case). Thermal stability is important to ensure that the adhesives remain stable during processing, storage, shipment, etc. In brief, 100 mg adhesive samples were heated to 160° C. under vacuum over 1 hour, then allowed to cool under vacuum for another hour before their final masses were determined. Thermal stability/volatiles content was taken as the difference is mass before and after heating.

TABLE 1d

Analysis of Adhesive Compounds

| Adhesive | % Volatiles content (mass loss at 160° C.) |
|---|---|
| Compound 1 | 1.2 ± 0.6 |
| Compound 2 | 1.1 ± 0.2 |
| Compound 3 | 1.1 ± 0.2 |
| Compound 4 | 0.8 ± 0.1 |
| Compound 5 | 1.1 ± 0.2 |
| Compound 6 | 0.0 ± 0.0 |
| Compound 7 | 0.4 ± 0.0 |

Example 8. Analysis of Adhesive Aqueous Solubility and Swelling

The solubility and swelling potential of the adhesive compounds was evaluated. In brief, 0.200 g adhesive samples of were dried under vacuum at 40° C. over 48 h and then weighed to obtain their initial dried mass. 25.0 mL of deionized water was added to each sample, and samples were incubated at room temperature (approximately 21° C.) for 48 h with intermittent mixing. After 48 h, the aqueous phase was decanted, lyophilized, and then vacuum dried overnight at 40° C. in order to determine the mass of material extracted into the water. The ratio of extracted material to the mass of aqueous solution was used to estimate aqueous solubility of each adhesive. The swelling of the residual adhesive, taken as the mass percent of water gained relative to initial adhesive mass, was determined by removing excess water with a kimwipe prior to massing the sample post-incubation. Table 2 shows the solubility and swelling potential of the adhesive compounds.

TABLE 1

Solubility and Swelling Potential of Adhesive Compounds.

| | m(Sample) (g) | | Extractable Mass (g) | | Estimated Solubility in diH2O (mg/g) | | Swelling - H2O Mass Gain (%) | |
|---|---|---|---|---|---|---|---|---|
| Adhesive | Ave | St Dev | Ave | St Dev | Ave | St Dev | Ave | St Dev |
| Compound 1 | 0.2184 | 0.0224 | 0.0040 | 0.0017 | 0.16 | 0.07 | 43.6 | 32.5 |
| Compound 2 | 0.2657 | 0.0084 | 0.0161 | 0.0022 | 0.66 | 0.09 | 98.6 | 8.5 |
| Compound 3 | 0.2068 | 0.0175 | 0.0000 | 0.0002 | 0.00 | 0.01 | 10.3 | 8.1 |
| Compound 4 | 0.2300 | 0.0125 | −0.0006 | 0.0016 | −0.02 | 0.06 | 18.3 | 1.8 |
| Compound 5 | 0.3668 | 0.0672 | 0.0009 | 0.0003 | 0.04 | 0.01 | 6.3 | 2.4 |
| Compound 6 | 0.3357 | 0.0933 | −0.0002 | 0.0003 | −0.01 | 0.01 | 1.9 | 1.9 |
| Compound 7 | 0.2358 | 0.0310 | 0.0003 | 0.0000 | 0.01 | 0.00 | 4.8 | 5.4 |
| Blank | 0.0000 | 0.0003 | 0.0000 | 0.0000 | 0.00 | 0.00 | NA | NA |

All the adhesives tested evidently have low aqueous solubility; the highest average solubility was less than 1 mg/g of water (0.66 mg/g for Compound 2). However, the majority of adhesives tested exhibited solubilities an order of magnitude lower. In two cases (Compounds 4 and 6), the extractable mass was too small to reliably register.

Example 9. Analysis of Thermal Properties of Adhesives

The glass transition temperatures and/or the melting temperatures of the pure adhesives were obtained from Differential Scanning calorimetry (DSC) experiments performed on a DSC7020 Thermal Analysis system (Hitachi High Technologies Canada Inc., ON, Ca) equipped with an electric cooling system. Samples (5-15 mg) were loaded into open 40 μL aluminium DSC pans, and introduced into the DSC sample chamber which was continuously purged with a dry nitrogen flow at 40 mL/min. Each sample was equilibrated at 150° C. for 5 minutes to erase thermal history, cooled to −90° C. at a rate of 20° C./min, held isothermally for 5 min, heated again to 150° C. at a rate of 5° C./min, held isothermally for 5 min, then cooled again to −90° C. at a rate of 5° C./min, held isothermally for 5 min, and finally heated again to 180° C. at a rate of 5° C./min. The melting ($T_M$) and/or glass transition ($T_g$) temperatures were calculated from the thermograms using the Software for NEXTA Standard Analysis, v2.0. The Thermal properties of pure adhesives and adhesive blends are provided in Table 4.

The tackifying temperatures of the pure adhesives were determined as follows. 100 mg adhesive samples were placed in scintillation glass vials and equilibrated to 5 mins in a water bath at room temperature (23° C.). The temperature of the water bath was increased to 75° C. at 1° C./min using the rate-programmable feature of the heating plate. The tackifying temperature was taken at the temperature at which the adhesive changed from a non-flowing rigid/glassy state to a viscous amorphous state that just stringed when prodded with a pipette. Results are presented in Table 3.

TABLE 3

Glass transition temperatures and/or melting temperatures of pure adhesives as obtained from DSC experiments, and tackifying temperatures of the same adhesives.

| Pure Adhesives | $T_g$ (° C.) | Tackifying temperature (° C.) |
|---|---|---|
| Compound 1 | 25.9 ± 1.9 | 40.0 ± 0.6 |
| Compound 2 | 40.8 ± 3.5 | 44.0 ± 1.0 |
| Compound 3 | 52.5 ± 1.5 (Tm) | 49.0 ± 1.0 |
| Compound 4 | 45.7 ± 0.2 | 47.2 ± 0.4 |
| Compound 5 | −10.3 ± 0.3 | 25.0 ± 0.2 |
| Compound 6 | −42.2 ± 5.6 | 29.0 ± 0.5 |
| Compound 7 | 14.7 ± 0.5 | 40.6 ± 0.6 |

Example 10. Analysis of Adhesive Strength

The lap shear strength of the adhesives was obtained by performing standard lap shear tests using an Instron universal testing machine in tensile mode with a 1000 N load cell and a 25 mm/min applied strain rate. Samples (n=6) comprised of adhesive sandwiched between aluminum substrates with a 2×1 $cm^2$ contact area and incubated at room temperature overnight prior to testing. The results are provided in Table 4.

TABLE 4

Lap Shear Strength of Adhesives.

| Adhesive | Lap shear strength (kPa) |
|---|---|
| Compound 1 | 3091 ± 725 |
| Compound 2 | 3423 ± 906 |
| Compound 3 | 3175 ± 557 |
| Compound 4 | 2359 ± 433 |
| Compound 5 | 1743 ± 297 |
| Compound 6 | 490 ± 192 |
| Compound 7 | 6089 ± 1609 |

Example 11. In Vitro Cell Cytotoxicity

In vitro cell cytotoxicity of Adhesive compounds 4, 6 and 7 as well as the polymer film and the tape device were tested by WST assay. Materials were extracted in growth media (DMEM) at a concentration of 10 mg/mL for compounds and 7 $mm^2$/mL for polymer film and device. Positive and negative controls were treated with 5% DMSO and growth media, respectively. Cells were seeded at the density of 10,000 cells per well. Cell viability was measured after 24 and 72 hours of contact of materials with A10 cells. All materials showed cell viability above the minimum 70% cell viability required for FDA submission except for Compound 4 which had approximately 10% cell viability at both timepoints (FIG. 1). Cytotoxicity of materials was analyzed by direct contact with A10 cells for 24 and 72 hours in comparison to negative and positive controls (DMEM and 5% DMSO, respectively). Cell viability (%) values were determined by WST-1 colorimetric assay. Results are expressed as mean±standard deviation; n=4.

Example 12. Influence of Adhesive Composition on Device Performance

Figure 2:
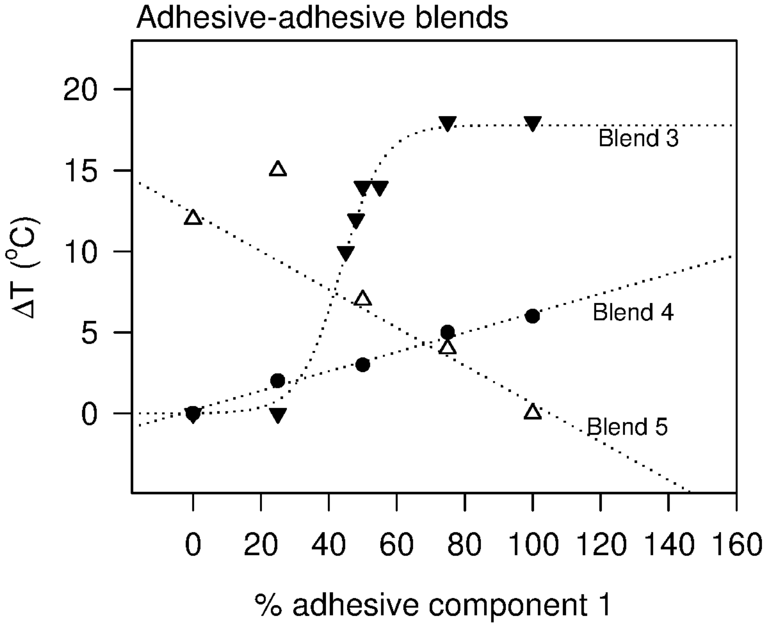
FIG. 2 is a graph showing change in tackifying temperature (normalized to the temperature of the adhesive with the lowest tackifying temperature) of adhesives upon blending with other adhesive compounds.

Adhesive performance could be tuned by varying the composition of the adhesive component. This, however, is not a trivial task, as can be seen in FIG. 2 by the non-similar and, therefore, non-obvious dependence of adhesive properties such as tackifying temperature (FIG. 2) on different adhesive components.

Tackifying temperatures and adhesive properties of adhesive-adhesive blend mixtures were evaluated. Blends were prepared by hot mixing select weight ratios of the adhesive components together. 100 mg adhesive samples were placed in scintillation glass vials and equilibrated to 5 mins in a water bath at room temperature (23° C.), following which the temperature of the water bath was increased to 75° C. at 1° C./min using the rate-programmable feature of the heating plate. The tackifying temperature was taken at the temperature at which the adhesive mixture changed from a non-flowing solid to a viscous amorphous state that just stringed when prodded with a pipette. Adhesive properties were determined on adhesive films obtained using an Auto C-PL, H laboratory press (Carver Inc, USA). Approximately 0.1 g of adhesive was placed between Teflon liners and left on the press for 5 min to thermally equilibrate to the 80° C. set temperature. Samples were then compressed at 80° C. for 5 min under a 600 kg load, removed from the press, and given 20 min to cool to room temperature. The Teflon liners were then separated in order to observe the adhesive blends. Adhesive blends were evaluated qualitatively for 1) adhesion to the Teflon and tackiness of the film, 2) stiffness/plasticity/brittleness by bending the Teflon and observing the film for cracking, and 3) cohesion of the film as it was peeled from the Teflon surface.

Table 5 describes the influence of adhesive-adhesive blends, Table 5 shows the influence of the polymer filler within the adhesive blend, and Table 7 shows the influence of particulate adhesives with the adhesive blend.

TABLE 5

Tackifying Temperatures and Adhesive Properties of Adhesive-Adhesive Blend Mixtures.

| Blend | Composition | Mass ratio | Tackifying temperature (° C.) | Adhesion | Brittleness/ Stiffness | Cohesion |
|---|---|---|---|---|---|---|
| 5a | Compound 6: Compound 7 | 25:75 | 44 | adheres, tacky | — | good cohesion, peels |
| 5b | Compound 6: Compound 7 | 50:50 | 36 | adheres, tacky | — | good cohesion, peels |
| 5c | Compound 6: Compound 7 | 75:25 | 33 | adheres, tacky | no cracks, elastic | — |
| 3a | Compound 4: Compound 6 | 25:75 | 29 | adheres, tacky | — | poor cohesion, no peel |
| 3d | Compound 4: Compound 6 | 50:50 | 43 | adheres, tacky | — | poor cohesion, no peel |
| 3f | Compound 4: Compound 6 | 75:25 | 47 | strong adhesion, no tack | brittle-cracks | — |
| 7a | Compound 4: Compound 6: PCL | 37.5:12.5:50 | 49 | poor adhesion (delamina ted) | stiff, brittle | peels |
| 7b | Compound 4: Compound 6: PCL | 25:25:50 | 48 | adheres | some stretch, but crazes | peels |
| 7c | Compound 4: Compound 6: PCL | 12.5:37.5:50 | 46 | adheres | tears with little stretch | no peel |
| 8a | Compound 6: Compound 7: PCL | 37.5:12.5:50 | 44 | adheres, no tack | no cracks | poor cohesion, tears w peel |
| 8b | Compound 6: Compound 7: PCL | 12.5:37.5:50 | 47 | adheres, no tack | no cracks, elastic | peeled as whole sheet |
| 8c | Compound 6: Compound 7: PCL | 25:25:50 | 46 | adheres, no tack | no cracks, elastic | peeled as whole sheet |

We evaluated the influence of polymer filler on performance of bone tape Device C, wherein the adhesive component comprises 50% w/w % of adhesive Blend 4a and 50% of the listed polymer filler, and the support side comprises Polymer 3. The bone tape Device was applied using an ultrasonic energy source onto a zygoma covered in citrated horse blood prior to application in order to mimic in vivo application. Tape performance was assessed qualitatively looking at tape adhesion, ease of application, peel strength, and tensile strength, wherein a score of 0=no adhesion to bone, 5=good application and adhesion to bone and good tensile or good peel strengths; and 10=desirable adhesion, peel resistance and tensile strength. The results are provided in Table 6.

TABLE 6

Influence of Polymer Filler on Performance of Bone Tape Device C.

| Bone Tape | Polymer filler | Ave Score/10 | Tg/Tm of polymer filler (° C.) | Comments |
|---|---|---|---|---|
| Device C-1 | — | 3 | 43 (Tg) | applies well, poor peel and tension; very brittle |
| Device C-2 | PCL50 | 5 | 60 (Tm); 87 J/g | Applies easily, sticks, mitigates against fluid buildup under bone, poor peel, and good strength. Not brittle |
| Device C-3 | PLC7015 | 1 | 22.8 (Tg) | Does not stay stuck to bone upon removal of applicator |
| Device C-4 | LG824s | 0 | −12 (Tg1); 27.5 (Tg2); 56.5 (Tg3), 155 (Tm1); 160 (Tm2) | Does not stick |
| Device C-5 | L210s HA | 0 | 60 (Tg)*; 180 (Tm)* | Does not stick |
| Device C-6 | PCL14 | 3 | 60 (Tm)* | applies well, poor peel and tension, brittle |
| Device C-7 | Compound 3 | 6.5 | 51 (Tm); 40 J/g | Applies well; good peel and tension, brittle |
| Device C-8 | PF127 (pluronic acid) | 3 | 57 (Tm)* | applies ok; swells and detaches from backing/bone, brittle |
| Device C-9 | HA | 3 | 1100 (Tm)* | applies well, poor peel and tension, brittle |
| Device C-10 | PBA (poly(1,4-butylene adipate)) | 5 | −68 (Tg)*; 54 (Tm)* | Applies well; good peel; poor tension, not brittle |

Table 6 shows that polymer fillers may be used to improve adhesive performance. Without wishing to be bound by theory, this occurs if the polymer filler positively impacts the physical and/or mechanical properties of the adhesive, thereby functioning as a second phase strengthener. For example, polymer fillers with too low (e.g. PLC7015) or too high (e.g. LG824s, L210s HA) softening temperatures restrict the performance of the adhesive layer to below that of the control adhesive (no fillers) itself. Higher molecular weight polymers present improved tensile resistance (e.g. PCL50 versus PCL14, PBA), whilst flexible polymers (e.g. PBA) contribute to improved peel performance. Inorganic fillers, e.g. HA, do not provide the same level of second phase strengthening as the compatible polymer fillers do. Without wishing to be bound by theory, inorganic particulates are typically void fillers, whereas polymer fillers contribute to improved elongation/tensile properties on account of their long chain entanglement interactions.

Polymers which are not miscible with the adhesive compounds (evidenced from distinct adhesive and polymer Tg domains on DSC thermograms), e.g. LG824s and L210s HA, also do not work well, likely because their phase strengthening mechanism is reduced to primarily void filling in the absence of the chain entanglement and the associated intermolecular interactions which are facilitated by phase mixing of the polymer phase with the adhesive compounds. This is corroborated by Device C-7 (Table 6) which shows that the highest scores are obtained when another adhesive compound with suitable mechanical and/or physical properties is incorporated into the adhesive layer as the polymer filler component.

Polymer fillers which increase the overall hydrophilicity of the adhesive layer, e.g. PF127, will increase the swelling capacity and/or solubility of the adhesive layer, leading to the eventual failure of bone tape via detachment from bone and/or the side support. On the other hand, polymer fillers which decrease the hydrophilicity of the adhesive layer (e.g. PCL) are desirable to mitigate against bone tape failure due to water ingress in vivo.

Example 13. Influence of Particulate Additives on Bone Tape Device Performance

We evaluated the influence of particulate additives on bone tape Device D and Device F performances. Varying amounts of the listed particulates were mixed into adhesive formulations comprising 50 wt % of Adhesive Blend 4a or Adhesive Blend 9a, and 50% of a polymer filler and assessed for application and adhesion to rabbit zygoma. The bone tape Device was applied using an ultrasonic energy source onto a zygoma covered in citrated horse blood. Wt % reflects amount of inorganic particulate added relative to the adhesive formulation organic mass. Tape performance was assessed qualitatively looking at tape adhesion, ease of application, peel strength, and tensile strength, wherein a score of 0=no adhesion to bone, 5=good application and adhesion to bone and good tensile or good peel strengths; and 10=desirable adhesion, peel resistance and tensile strength. The results are provided in Table 7.

TABLE 7

Influence of Particulate Additives on Bone Tape Device Performance.

| Bone Tape | Additive | wt % | Ave Score/10 | Polymer filler |
|---|---|---|---|---|
| Polymer 1 | — | 0 | 0 | $PCL_{50}$ (100%) |
| Device D-1 | none | 0 | 6 | $PCL_{50}$ |
| Device D-2 | NaCl | 1.25 | 4.3 | $PCL_{50}$ |
| Device D-3 | $Na_2CO_3$ | 2.5 | 5 | $PCL_{50}$ |
| Device D-4 | NaCl | 2.5 | 5.5 | $PCL_{50}$ |
| Device D-5 | $SiO_2$ | 2.5 | 5.8 | $PCL_{50}$ |
| Device D-6 | NaCl | 5 | 7.5 | $PCL_{50}$ |
| Device D-7 | HA (pH 11) | 5 | 6.3 | $PCL_{50}$ |
| Device D-8 | NaCl | 10 | 5.5 | $PCL_{50}$ |
| Device D-9 | HA (pH 11) | 20 | 6.25 | $PCL_{50}$ |
| Device D-10 | HA (pH 11) | 30 | 7 | $PCL_{50}$ |
| Device D-11 | HA (pH 11) | 40 | 7.3 | $PCL_{50}$ |
| Device D-12 | HA (pH 11) | 60 | 9.3 | $PCL_{50}$ |
| Device D-13 | HA (pH 11) | 100 | 5.5 | $PCL_{50}$ |
| Device D-14 | HA (pH 11) | 60 | 3.5 | PBA |
| Device D-15 | HA (pH 11) | 60 | 7.5 | PES |
| Device D-16 | HA (pH 11) | 60 | 4 | PEA |
| Device D-17 | TTCP | 60 | 7.5 | $PCL_{50}$ |
| Device F-1 | HA (pH 11) | 80 | 9.5 | $PCL_{50}$ |
| Device F-2 | HA (pH 7) | 80 | 9.25 | $PCL_{50}$ |
| Device F-3 | HA (pH 5) | 80 | 8.5 | $PCL_{50}$ |
| Device F-4 | TTCP | 80 | 7 | $PCL_{50}$ |
| Device F-5 | DCP | 80 | 7.5 | $PCL_{50}$ |
| Device F-6 | HA (pH 11) | 80 | 7.75 | $PCL_{50}$/PBA 25:75 |
| Device F-7 | HA (pH 7) | 80 | 7 | $PCL_{14}$:$PCL_{45}$:$PCL_{80}$ 33:33:33 |
| Device F-8 | HA (pH 7) | 80 | 9 | $PCL_{50}$:PLA-co-PCL 90:10 |

The addition of additives at concentrations less than 2.5 wt % result in no benefit or decreased performance. Additive levels at 2.5 wt % resulted in easier application of tape but no increase in performance was observed. Additive levels at 5-10% resulted in enhanced application and fluid displacement but strength was not noticeably improved. Without wishing to be bound by theory, it is hypothesized that when present in suitable amounts, these additives aid in energy transfer from the backing to the adhesive component, allowing the adhesive component to reach its tackifying temperature without compromising the support side component of bone tape.

Using soluble additives above 10 wt %, however, results in bone tape with compromised integrity upon application as the soluble additive components become dissolved or leached out, leaving behind craters/voids in the bone tape. On the other hand, insoluble additives, e.g. HA, and TTCP, at levels of 20 wt % and above result in improved tensile strength and application compared to controls. Without wishing to be bound by theory, this may be attributed to the ability of non-soluble additives to function as void filling second phase strengthening agents in addition to aiding with energy transfer from the support to the adhesive component during application. Evidence for the role of these particulate additives as void filling second phase strengthening agents can be elucidated from a comparison of devices D-12 against D-14 through D-16 in Table 7, of Device F-1 with F-6, and of Device F-2 with F-7 and F-8, which all show that for a given HA content, the nature of the polymer filler within the adhesive strongly influences the effectiveness of the additive (note that except for PES, the polymer fillers in all of these devices all present similar melting points). Further evidence can be seen in Device F-2 versus F-4, wherein the more porous but compositionally similar TTCP filler makes for a less effective void filling agent compared to HA.

Devices F-1 through F-3 in Table 7 shows the influence of additive pH on device performance. From the prior art, it is known that basic additives induce in situ crosslinking of the catechol moieties of catechol-containing adhesives. This is also apparent in the adhesive devices of this embodiment; residual reactants in the HA additives impart an effective non-neutral pH of the additive. We have found that the effective pH of HA can range from acidic to basic based on the supplier's manufacturing method. When used as-is in the manufacture of bone tape, without further washing to remove the non-neutral impurities, an HA presenting basic pH properties results in in situ pH-induced catechol-catechol crosslinking and/or dimerization under the high-temperature processing conditions of bone tape manufacture. As shown in Table 7 for the devices of this embodiment, however, whilst some improvements in bone tape performance can be had in those devices wherein the adhesives undergo in situ crosslinking/oligomerization (e.g. Device F-1), it is also clearly apparent that these improvements are only marginal (e.g. Device F-2 and F-3). These results reinforce that the adhesives of this embodiment do not require crosslinking for desired adhesive and/or device performance. Further, in the presence of said in situ-induced adhesive crosslinking, the resulting bone tapes are least aesthetically pleasing; with increasing pH-induced crosslinking, the color of adhesive and the resulting bone tape shifts from white towards dark brown/black. Thus, non-crosslinked adhesive devices of the present embodiment, manufactured using particulate additives with pH 7, meet desired aesthetic and performance criteria for use in surgical interventions.

Bone tape with adhesive layers comprising of only the filler polymer PCL, void of adhesive or additives, does not stick to bone.

Example 14. Influence of Support Composition on Bone Tape Device Performance

The influence of support side composition was investigated on bone tape Device E. Device E, comprising adhesive Blend 6f on various support side compositions were prepared and assessed for application and adhesion to rabbit zygoma. Application was performed using an ultrasonic heating system. Zygoma was covered in citrated horse blood prior to application in order to mimic in vivo application. Tape performance was assessed qualitatively looking at tape adhesion, ease of application, peel strength, and tensile strength, wherein Y=yes; N=no; and a score of 0=fails, 3=average; and 5=very good performance. The results are provided in Table 8.

TABLE 8

Influence of Support Side Composition on Bone Tape Device E.

| | bone tape assessment | | | | | polymer properties | | | |
|---|---|---|---|---|---|---|---|---|---|
| | | Application | | Post-application | | | | | Glass |
| | Adhesion | Backing | Adhesive | | | Strength | Modulus | Melting Temperature | Transition Temperature |
| Support side | to bone | melts | flows out | Tension | Peel | [MPa] | [GPa] | [° C.] | [° C.] |
| Polymer 1 (PCL) | Y | Y | N | 2 | 4 | 15 ± 1 | 0.2 | 55-60 | — |
| Polymer 2 (PDX) | Y | Y | N | 3 | 3 | 28 ± 1 | 0.4 ± 0.1 | 110 | −16 |
| Polymer Blend 3 (PDX/PCL, 60/40) | Y | N | N | 3 | 3 | 18 ± 4 | 0.6 ± 0.1 | 110, 55 | −16 |
| Polymer 5 (LG824s) | Y | N | Y | 5 | 1 | 63 ± 2 | 2.0 ± 0.2 | | 55 |
| Polymer Blend 6 (LG824s/PLC7015, 60/40) | Y | N | N | 5 | 3 | 25 ± 3 | 0.9 ± 0.1 | | 42 |
| Polymer 7 (PLC9517) | Y | N | Y | 1 | 1 | 60.0* | 2.5* | 164 | 52 |
| Polymer 8 (PLC8516) | Y | Y | Y | 1 | 4 | 53 ± 1 | 1.6 ± 0.2 | | 42 |
| Polymer 9 (LG210 HA) | Y | N | N | 0 | 0 | 55* | 4.3* | 180* | 60* |

*indicates from manufacturer reported data

Table 8 shows that bone tape performance is strongly dependent upon the properties of the support side component.

Polymers which melt/soften below or at the tackifying temperature of the adhesive formulation (e.g. PCL, PLC7015) are not optimal when used on their own. In these situations, the challenge is the application of the bone tape without introducing defects into the support side component that would compromise the tensile strength of the device post-surgery. This is especially true for polymers such as PCL with significant crystalline content that undergo rapid melt at temperatures close to or below the tackifying temperature of the adhesive layer. This also applies to polymers which present polymorphic phase transitions and/or which contain multiple polymorphs with phase transitions at or below the tackifying temperature of the adhesive formulation; e.g., PDX presents a final melt temperature at 110° C., but also undergoes several polymorphic transitions inclusive of a melt-mediated recrystallization between room temperature and 50° C.

Polymers which melt/soften at too high temperatures relative to the tackifying temperature of the adhesive formulation (e.g. PLC9517) also present application challenges which translate into compromised device performance. For these systems, the significantly higher temperatures required to soften the support side component in order for it to conform to the shape of the bone surface and thus facilitate the full wetting of the bone surface by the adhesive component actually results in flow out of the adhesive from beneath the bone tape device, leading instead to a compromised device with poor adhesion characteristics. A similar challenge is also observed in polymers with too high elastic moduli ($E_{tensile}$>0.5 GPa; e.g. LG824s, PLC8516), which generally require heating well above their glass transition temperatures in order to improve their flexibility enough so that they could sufficiently contour to the shape of the bone.

Generally, polymers with desired melting profile, tensile strength, and/or elastic modulus could be obtained upon blending of individual polymers, e.g. Polymers 3 and 6 in Table 8 above. However, we note that support compositions which do not comprise PCL or copolymers containing PCL generally do not adhere well to the adhesive layer, even with manufacturing tweaks such as the introduction of texture on the support surface of the adhesive-support interface, or laminate-pressing protocols (Table 9). For example, pure PDX backings (Polymer 2) and LG824s (Polymer 5) backings result in delamination of the adhesive layers when the tapes are flexed, regardless of the introduction of texturing at the adhesive-support side interface (Table 9). On the other hand, in a polymer blend, despite being incompatible with nearly all other polymers, PCL (e.g. Polymer blend 3) and/or PCL-containing copolymers (e.g. Polymer blend 6) contribute to lower softening temperatures (Table 8), compatibility with the adhesive layers regardless of manufacturing method (Table 9), and strength retention due to its hydrophobicity (Table 10).

TABLE 9

| Influence of Adhesive-Support side compatibility on Bone Tape Performance. | | | | | | |
|---|---|---|---|---|---|---|
| | | | | | Bone tape assessment | |
| | | | Manufacturing | | Adhesive- | Overall |
| BoneTape | | | Textured | | backing | Performance/ |
| Device | Adhesive | Support | interface | Laminated | compatibility/5* | 10** |
| E-2 | Blend 6f | Polymer 2 (PDX) | N | N | 0.5 | ND |
| | | | Y | N | 2 | 5 |
| E-3 | Blend 6f | | N | N | | ND |
| | | Polymer blend 3 (PDX/PCL, 60/40) | Y | N | 5 | 4 |
| E-5 | Blend 6f | Polymer 5 (LG824s) | Y | N | 3.5 | 5 |
| E-6 | Blend 6f | Polymer blend 6 (LG824S/PLC7015, 60/40) | Y | N | 4.5 | 5 |
| F-5 | Blend 9c | Polymer 5 (LG824s) | N | N | 1.5 | 7.25 |
| | | | Y | N | 1 | 8.25 |
| | | | N | Y | 1 | 8.1 |
| | | | Y | Y | 1 | 7.3 |
| F-2 | Blend 9c | Polymer blend 6 (LG824S/PLC7015, 60/40) | N | N | 3 | 8.25 |
| | | | Y | N | 4 | 9 |
| | | | N | Y | 4 | 9 |
| | | | Y | Y | 4 | 9 |

*Adhesive-Support side compatibility was assessed qualitatively based on a 180° flexibility test wherein a 0.5 × 1 $cm^2$ piece of bone tape was folded in half and scored as follows: 0 = adhesive does not adhere to support side; 1 = adhesive readily falls away from support side; 2 = adhesive separates from backing; 3 = adhesive separates from backing with picking; 4 = adhesive splits but does not delaminate from support side; 5 = adhesive layer inseparable from support side.

**Bone tape device performance was assessed qualitatively via application to rabbit zygoma covered in citrated horse blood using an ultrasonic heating system, wherein a score of 0 = no adhesion to bone, 5 = good application and adhesion to bone and good tensile or good peel strengths; and 10 = desirable adhesion, peel resistance and tensile strength.

TABLE 10

Mechanical properties of select PCL-containing polymer blends over 7 weeks under physiological conditions in order to assess their utility for long term use in in vivo settings. Tensile specimens were cut using a laser cutter to approximately 0.5 cm and assessed using a modified ASTM D882-18 standard.

| | t = 0 w | | | | t = 3 w | | | | t = 7 w | | | |
|---|---|---|---|---|---|---|---|---|---|---|---|---|
| | Tensile Strength (MPa) | | Elastic Modulus (GPa) | | Tensile Strength (MPa) | | Elastic Modulus (GPa) | | Tensile Strength (MPa) | | Elastic Modulus (GPa) | |
| Material | Ave | StD | Ave | StD | Ave | StD | Ave | StD | Ave | StD | Ave | StD |
| Polymer Blend 10 | 24.27 | 0.49 | 0.63 | 0.03 | 25.22 | 0.47 | 0.73 | 0.01 | 21.94 | 1.67 | 0.83 | 0.05 |
| Polymer Blend 11 | 17.79 | 0.40 | 0.32 | 0.03 | 20.26 | 0.88 | 0.46 | 0.01 | 20.67 | 0.97 | 0.42 | 0.04 |
| Polymer Blend 12 | 18.09 | 0.42 | 0.44 | 0.02 | 20.86 | 0.81 | 0.24 | 0.04 | 20.75 | 2.84 | 0.57 | 0.06 |
| Polymer Blend 13 | 21.52 | 3.08 | 0.59 | 0.10 | 22.08 | 1.25 | 0.49 | 0.10 | 19.66 | 1.98 | 0.56 | 0.14 |

Example 15. Effect of Adhesive and Backing Thicknesses on the Performance of BoneTape BoneTape can be produced with varying backing thicknesses and adhesive thicknesses. Using the Adhesive blend 9c and the Polymer Blend 6 backing, several combinations of adhesive and backing thicknesses were used to examine the influence of component thickness on the performance of a laminated Device F-2. Using a 70 kHz ultrasonic welder set to an energy of 2.5 J, Device F-2 was applied onto a rabbit zygoma that was covered in citrated horse blood prior to application in order to mimic in vivo application. Tape performance was assessed qualitatively looking at tape adhesion, ease of application, peel strength, and tensile strength, wherein a score of 0=no adhesion to bone, 5=good application and adhesion to bone and good tensile or good peel strengths; and 10=desirable adhesion, peel resistance and tensile strength.

TABLE 11

| Influence of component thickness on Device F-2 performance. | | | | | |
|---|---|---|---|---|---|
| Backing Thickness/mm | Adhesive Thickness/mm | Overall Performance/10 | Flexibility/5 | Peel/5 | Tension/5 |
| 0.31 | 0.16 | 7.8 | 1.0 | 2.0 | 5.0 |
| 0.20 | 0.16 | 8.5 | 2.5 | 3.5 | 5.0 |
| | 0.05 | 8.9 | 4.5 | 3.0 | 5.0 |
| 0.12 | 0.16 | 8.5 | 3.0 | 3.0 | 5.0 |
| | 0.05 | 9.0 | 4.5 | 3.5 | 4.5 |
| 0.05 | 0.16 | 8.1 | 4.5 | 3.5 | 4.0 |
| | 0.05 | 7.6 | 5.0 | 3.0 | 2.5 |

Table 11 shows that a very thick support side polymer (0.31 mm) limits the flexibility and performance of the tapes, whilst the very thin backings also limit the performance of the tapes but greatly improved their flexibility. On the other hand, reducing the thickness of the adhesive layers improves the flexibility of the tapes while maintaining a similar performance score. Thus, tapes with thinner adhesives and/or support side layers are more suitable for applications requiring greatest flexibility, whilst tapes with the thicker support side layers will provide greatest stability/strength reinforcement to the tape.

Without wishing to be bound by theory, peel improves as a result of increased energy transfer from the support polymer into the adhesive layer when either the support layer is thinner or the adhesive is thinner. When the support layer is thinnest, the thermal energy lost to the support layer is least; and when the adhesive layer is thinnest, regardless of the energy transfer efficiency, the least amount of energy is required to melt the adhesive.

Example 16. Influence of Energy Application on Bone Tape Device Performance

As shown in examples 12 through 15, the selection of adhesive components, inclusive of fillers and/or particulate additives, as well as the selection of support side components, must be carefully and non-trivially coordinated in order to obtain optimal device properties and performance. In addition to the choice of device components, however, bone tape performance is also linked to the method of application. Table 12 shows the success of various applicators in the application of bone tape, Table 13 shows the resulting temperature profile during ultrasonic welding onto bone, Tables 14-15 show the influence of the ultrasonic device frequency on the surgical flow properties such as weld time and weld force to achieve desired BoneTape performance, Table 16 shows the dependence of the ultrasonic application on BoneTape composition and thickness, and Table 17 shows the useability of the welder at different application styles. In all instances except where otherwise stated, BoneTape application was performed using a 70 kHz ultrasound welder on a rabbit zygoma that was covered in citrated horse blood prior to application in order to mimic in vivo application, and tape performance was assessed qualitatively looking at tape adhesion, ease of application, peel strength, and tensile strength, wherein a score of 0=no adhesion to bone, 5=good application and adhesion to bone and good tensile or good peel strengths; and 10=desirable adhesion, peel resistance and tensile strength.

TABLE 12

Influence of energy source on bone tape performance. BoneTape Device F-2 was applied to the zygoma using different heat sources, then manually pulled off the bone in order to gauge the degree of adhesion, and rated on a qualitative scale from 1 to 5, wherein 1 = no adhesion under any circumstances, and 5 = excellent adhesion and application. In all cases, the heated BoneTape was applied by working/pressing it onto the substrate. Application energy (ultrasound), time (heat gun, heat lamp, UV lamp), or temperature (soldering iron) were sequentially increased until BoneTape failure occurred in order to assess the full potential of each method.

| Method of application | Score | Comments |
|---|---|---|
| Ultrasound | 4.5 | <1.5 J: requires multiple consecutive welds for adhesion<br>1.5-5 J: Adhesion was very good.<br>≥7 J: Good adhesion, but support polymer damages. |
| Heat gun | 2 | <15 sec: tape does not conform<br>15 sec: tape conforms well to the bone surface, but adhesion was minimal.<br>>15 sec: Shadowing, contamination (blowing), burn hazard, little control |
| Heat lamp | 2 | <10 sec: no adhesion<br>10-20 sec: tape conforms well to the bone surface, but adhesion was poor.<br>>20 sec: Shadowing, burn hazard, little control |
| Soldering iron | 1 | <82° C.: no adhesion.<br>82-115° C.: the tape conformed to the bone surface, but did not adhere.<br>>115° C.: Support polymer damages; burn hazard. |

Table 12 shows the superior performance of BoneTape when applied with ultrasonic energy as compared to any of the other energy sources investigated. Without wishing to be bound by theory, this success is attributed the ultrasound welder's ability to selectively melt or soften the adhesive layer relative to the support polymer layer in situ during the tape application. This selective in situ melting, combined with the constant vibrational forces of the ultrasound under the applied weld forces of the application acted concurrently to displace fluids as well as drive adhesive layer further into bone pores, resulting in the excellent adhesion properties observed. Conversely, the other methods presented non-discriminatory loss of thermal energy to the environment, which necessitated longer heating times and/or higher heating temperatures in order to make the tape conformable and/or the adhesive tacky. In addition to the longer heating times and/or higher heating temperatures, the non-discriminatory loss of thermal energy to the environment presented increased opportunities for both damage of the support polymer layer as well as tissue damage due to excessive/concentrated heating during application. Thus, for tape application using these alternate methods, it was necessary to heat the tape prior to application in order to avoid casting a "shadow" over the tape and to avoid burns, resulting in non-optimal surgical workflow processes or times. On the other hand, the ultrasonic welder presented desired adhesion with relatively short weld cycles (<1 sec per weld), and at weld energies less than 7J, it did not reach or sustain weld temperatures that could result in tissue damage or necrosis (Table 13). For the 70 kHz welder used in these experiments, however, an energy setting of 7J was typically too high, resulting in bone damage upon BoneTape application. This was apparent as bleaching of the bone where it came in contact with the welder and was attributed to excessive heating of the bone during the application which resulted in dehydration. However, charring of the bone was never observed under these conditions, indicating that the welder did not reach and/or sustain the temperatures during application that would result in thermal necrosis of healthy bone. Further, as shown in Table 13, the severity of this heat exposure under such aggressive conditions can be mitigated by increasing the times between consecutive welds.

TABLE 13

Ultrasound welding temperature profile during application of BoneTape Device F-2 onto wet zygoma bone using the 70 kHz ultrasonic welder. The temperature profile of bone near an application site was characterized ex vivo using a fine tipped type E thermocouple. To achieve this, a half zygoma (transected) was dissected out of a rabbit carcass, and a small hole (0.69 mm dia.) was drilled into the edge in order to accommodate the thermocouple tip (0.47 mm dia.). Given a bone thickness of 2.28 mm, the nominal distance from the bone surface to the thermocouple was about 0.9 mm. After dampening the bone with deionized water, BoneTape Device F-2 was applied to the zygoma directly over top of the probe tip using either 2.5 J or 7 J per weld. Temperature profiles was logged at 1 second intervals for each of 4 conditions: a single weld, 5 consecutive welds, 10 consecutive welds, and 5 welds spaced 5 seconds apart.

| | Condition | $T_{init}$ (° C.) | $T_{max}$ (° C.) | T rise (° C.) | T rise per weld (° C.) | Weld period (s) | Average time between welds (s) |
|---|---|---|---|---|---|---|---|
| 2.5 J | 1 Weld | 20 | 26 | 6 | 6 | ~1 | NA |
| | 5 Welds | 21 | 48 | 27 | 5.4 | 10 | 2 |
| | 10 Welds | 21 | 68 | 47 | 4.7 | 15 | 1.5 |
| | 5 welds, 5 sec intervals | 21 | 37 | 16 | 3.2 | 30 | 6 |
| | Continuous to 70° C. | 22 | 52 | 74 | NA | 9 | NA |
| 5 J | 1 Weld | 19 | 32 | 13 | 13 | ~1 | NA |
| | 5 Welds | 20 | 56 | 36 | 7.2 | 7 | 1.4 |
| | 5 welds_5 sec space | 21 | 58 | 37 | 7.4 | 30 | 6 |
| 7 J | 1 Weld | 20 | 31 | 11 | 11 | ~1 | NA |
| | 5 Welds | 20 | 71 | 51 | 10.2 | 9 | 1.8 |
| | 5 welds_5 sec space | 21 | 69 | 48 | 9.6 | 31 | 6.2 |

Tables 14 and 15 elucidates further the dependence of BoneTape's surgical work flow application on the ultrasound welding parameters.

TABLE 14

Dependence of surgical workflow (weld time and/or weld force) on ultrasonic frequency; in vitro proof of concept. The ability of 35 kHz and 70 kHz ultrasonic welding to apply BoneTape Device D-12 to Sawbones was investigated using horns matched with respect to cross-sectional area and surface finish (i.e. knurling). The ultrasonic horn was mounted upside down with the weld piece placed on top, and weld forces between 0.5N and 5.5N were applied using a linear guide and calibration masses. Welds were qualitatively evaluated for quality, primarily adhesion and backing damage.

| Weld Force | 35 kHz unit @ 100% Amplitude | | | | 70 kHz unit @1.5 J | |
|---|---|---|---|---|---|---|
| | | | | | High | Low |
| (N) | 1.5 J | 6 J | 12 J | 24 J | Amplitude | Amplitude |
| 0.5 | No | No | No | No | Okay | Okay |
| 1.0 | No | No | No | Okay | Good | Good |
| 1.5 | No | Poor | Poor | Good | Good | Good |

TABLE 14-continued

Dependence of surgical workflow (weld time and/or weld force) on ultrasonic frequency; in vitro proof of concept. The ability of 35 kHz and 70 kHz ultrasonic welding to apply BoneTape Device D-12 to Sawbones was investigated using horns matched with respect to cross-sectional area and surface finish (i.e. knurling). The ultrasonic horn was mounted upside down with the weld piece placed on top, and weld forces between 0.5N and 5.5N were applied using a linear guide and calibration masses. Welds were qualitatively evaluated for quality, primarily adhesion and backing damage.

| | | | | | 70 kHz unit @1.5 J | |
|---|---|---|---|---|---|---|
| Weld Force | 35 kHz unit @ 100% Amplitude | | | | High | Low |
| (N) | 1.5 J | 6 J | 12 J | 24 J | Amplitude | Amplitude |
| 2.5 | No | Poor | Okay | Good | Good | Good |
| 5.5 | No | Okay | Excessive damage | Excessive damage | Good | Good |

TABLE 15

The application of BoneTape Device F-2 to wet bone using ultrasonic welding at 35 kHz and 70 kHz was investigated ex vivo; horns matched for cross-sectional area and surface finish were used to apply BoneTape Device F-2 to rabbit zygoma freehand, using either a 35 kHz or 70 kHz ultrasonic welding unit.

| Ultrasound frequency | Amplitude (% of Maximum) | Energy (J) | Adhesion |
|---|---|---|---|
| 35 kHz | 100 | 3.0 | No |
| | 100 | 5.0 | No |
| | 100 | 7.0 | Poor |
| | 100 | 9.0 | Okay |
| | 100 | 12.0 | Okay |
| | 100 | 14.0 | Good |
| 70 kHz | 70 | 4.0 | Yes - backing damage |
| | 80 | 3.0 | Good |
| | 80 | 2.0 | Poor |
| | 75 | 3.0 | Good |
| | 75 | 2.5 | Good |

Table 14 shows that the higher frequency welder applied BoneTape to Sawbones well with just 1.5 J of ultrasonic energy at any weld force between 1.0 N and 5.5 N. By contrast, the lower frequency welder was substantially more dependent on weld force. This indicates that lower frequency welders are very dependent upon the user's skill (i.e., applied force per weld), whereas the higher frequency welder presents desired application regardless of differences in the application force from user to user.

Both Table 14 and Table 15 also show that the lower frequency unit required more energy, and therefore substantially more time, to complete a weld compared to the higher frequency unit. Moreover, welds performed with the lower frequency unit were generally qualitatively weaker than those prepared with the 70 kHz unit. Since the melting of the adhesive is directly linked to the rate at which energy is supplied, i.e., its power, this result shows that below a given power limit, not enough energy is delivered to melt the adhesive layer within a given weld cycle, whilst at too high power, too much energy is transmitted during the weld cycle, resulting in melting and burn through of the support polymer. Overall, these results show that the higher frequency welder is more advantageous for improved surgical workflow, requiring reduced weld times and/or weld forces to achieve desired welding of bone tape to bone.

The above results also indicate that the ability of BoneTape to tolerate high welding powers are linked to improved procedural utility. Table 16 shows how BoneTape's compositional features influence its ability to tolerate high welding energies and, therefore, high welding powers.

TABLE 16

Influence of composition and thickness on the weldability of BoneTape Device F-2 at different welding energies.

| Backing Thickness/mm | Adhesive Thickness/mm | Energy | Performance/10 | Peel/5 | Tension/5 |
|---|---|---|---|---|---|
| 0.12 | 0.16 | 2.5 | 8.5 | 3.0 | 5.0 |
| | | 3.5 | 9.2 | 3.8 | 4.9 |
| | | 5.0 | 9.3 | 4.3 | 5.0 |
| | 0.05 | 2.5 | 9.0 | 3.5 | 4.5 |
| | | 3.5 | 9.4 | 4.0 | 4.8 |
| | | 5.0 | 8.7 | 3.8 | 4.0 |

TABLE 16-continued

| Influence of composition and thickness on the weldability of BoneTape Device F-2 at different welding energies. | | | | | |
|---|---|---|---|---|---|
| Backing Thickness/mm | Adhesive Thickness/mm | Energy | Performance/10 | Peel/5 | Tension/5 |
| 0.20 | 0.16 | 2.5 | 8.5 | 3.5 | 5.0 |
| | | 3.5 | 8.25 | 3.4 | 4.0 |
| | | 5.0 | 8.9 | 3.9 | 4.25 |
| | 0.05 | 2.5 | 9.2 | 3.5 | 5.0 |
| | | 3.5 | 9.1 | 4.0 | 4.5 |
| | | 5.0 | 9.5 | 4.25 | 5.0 |

* Control bone tape comprising no heat transfer additive

Table 16 shows that the energy tolerance of BoneTape generally increases with increasing adhesive and/or support polymer layers. For a given support polymer thickness, regardless of the adhesive thickness, increasing the energy could generally increase the performance of the tape, particularly in the peel score, up to a peak energy, after which further increases in the energy lead to a decrease in the overall scores of the tapes. The improvement in performance was most significant for the thinner adhesive layer, with peak energy also occurring sooner for the thinner adhesive layer compared to the thicker adhesive layer. That is, with less adhesive to melt, less energy is required to secure the device onto bone.

Further, Table 16 shows that while excellent adhesion and tension could be achieved with under-optimal energies, maximum peel was only obtained at peak energy. This indicates that the adhesive can form strong tensile bonds with the bone surface once sufficiently softened so as to conform and contact the bone surface without requiring the adhesive itself to become fully flowable. However, for optimal peel, the adhesive must become fully melted and flowable, thereby allowing it to flow into bone pores and/or eliminate fluids from the bone surface. Thus, peel strength appears to be a manifestation of both mechanical and physical bonds. At too high energies, the adhesive likely becomes too fluid such that it flows out of bone tape and is lost. The lower post-peak scores observed in BoneTape comprising the thinner adhesive layers corroborates this.

Table 17 shows the useability of the ultrasonic welder comprising different horn geometries at different application styles.

TABLE 17

Influence of horn geometry on surgical workflow and BoneTape Device F-2 performance. In all instances, BoneTape Device F-2 is applied onto wet the zygoma using the 70 kHz welder with the different horn geometries at 2.5 J, then manually pulled off the bone in order to gauge the degree of adhesion, and rated on a qualitative scale from 1 to 5, wherein 1 = no adhesion under any circumstances, and 5 = excellent adhesion and application. The stamp method refers to the application of BoneTape with the welder via a series of consecutive welding tacks normal to the application surface so as to cover the entire surface, whilst the paint method refers to the continuous sliding of the welder across the entirety of the tape surface in a painting/ brushstroke motion.

The horn textures described in Table 17 are defined as follows:

Fine: the individual texture elements are evenly spaced apart, with uniform depths of up to 0.127 mm which represent 30-80% of the total tape thickness.

Coarse: the individual texture elements are evenly spaced apart, with uniform depths ≥0.381 mm which represent 80-400% of the total tape thickness.

Sandblasted: the individual texture elements are non-uniformly shaped and distributed, with non-uniform depths less than 30% of the total tape thickness.

Smooth: no horn texture on the tip of the horn geometry.

Rounded: a smooth horn with no sharp edges.

| Technique | Horn texture | Score/5 | Comments |
|---|---|---|---|
| Stamp-method | Smooth | 2.5 | Slides, difficult to localize |
| | Sandblasted | 2 | Support polymer sticks to horn |
| | Coarse | 3 | Extreme polymer support damage and underlying bone |
| | Fine | 4.5 | works well |
| | Rounded | 1 | Point contact results in small contact area per weld Point contact also displaces anchor layer with applied force and energy |
| Paint-method | Smooth | 4 | works well |
| | Sandblasted | 2 | Support polymer sticks to horn; polymer builds up on surface, resulting in increased thermal losses; polymer damage |
| | Coarse | 1 | Extreme polymer support damage and underlying bone; can't slide |
| | Fine | 4 | works well |
| | Rounded | 2 | Point contact results in small contact area per weld Point contact also displaces anchor layer with applied force and energy |

As shown, BoneTape can be suitably applied using a variety of methods and/or horn geometries. Whilst some geometries are ill-suited for bone tape application via a given technique, for example, the coarse horn results in significant tape and/or bone damage when used in the painting motion, other geometries such as the fine geometry works well with any user preferred technique. Generally, the painting technique presents a steeper learning curve since the ultrasonic welder must be held normal to surface for application. However, stamping facilitates initial weld points to anchor BT whilst attachment occurs, making for a more desirable surgical workflow. Overall, these results show the flexibility of bone tape application towards variations in user techniques and, thus, increased procedural utility.

CROSS REFERENCE TO RELATED APPLICATIONS

This application is a continuation-in-part of U.S. application Ser. No. 17/340,313, filed on Jun. 7, 2021, which claims the benefit of priority from U.S. provisional application No. 63/194,297, filed on May 28, 2021, each of which are hereby incorporated by reference in their entirety.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features herein before set forth.

The invention claimed is:

1. A method for reversibly stabilizing bone fragments in a body, the method comprising:

(i) forming a first reversible anchor on a first bone fragment by (a) heating an adhesive composition to form a softened adhesive composition and contacting the softened adhesive composition to the first bone fragment, and (b) permitting the softened adhesive composition to cool to form the first anchor affixed to the first bone fragment;

(ii) forming a second reversible anchor on a second bone fragment by (a) heating an adhesive composition to form a softened adhesive composition and contacting the softened adhesive composition to the second bone fragment, and (b) permitting the softened adhesive composition to cool to form the second anchor affixed to the second bone fragment;

wherein the heating comprises applying ultrasonic energy using an ultrasonic welder at a frequency of from 35 kHz to 70 KHz;

wherein the adhesive composition comprises hydroxyapatite as a heat transfer agent, a filler comprising polycaprolactone (PCL), polydioxanone (PDX), poly(lactic-co-glycolic acid) (PLGA), or poly-3-hydroxybutyrate (P3HB), hydroxyapatite (HA), or a copolymer thereof, or a blend thereof, and the adhesive composition has a tackifying temperature from 40° C. to 55° C., and wherein the first anchor and the second anchor are connected to a support structure for stabilizing the bone fragments; and wherein the adhesive composition is not dependent upon in situ curing reactions for adhesion.

2. The method of claim 1, wherein the support structure is a flexible support comprising a biodegradable and biocompatible polymer linking the first anchor to the second anchor.

3. The method of claim 2, wherein the support structure, the first anchor, and the second anchor are formed from a tape comprising (x) a non-adhesive top layer that is the support structure, and (y) a bottom layer that is adhesive when softened to form the first anchor and the second anchor.

4. The method of claim 1, wherein the adhesive composition is not water soluble.

5. The method of claim 1, wherein the adhesive composition comprises a heat transfer agent.

6. The method of claim 5, wherein the heat transfer agent is present in an amount that permits the softened adhesive composition to cool and harden in 120 seconds or less or in 10 seconds or less.

7. The method of claim 5, wherein the heat transfer agent is present in an amount that permits the adhesive composition to soften within 120 seconds or less of applying energy or within 10 seconds or less of applying energy.

8. The method of claim 1, wherein the adhesive composition comprises a polymer of formula (I):

formula (I)

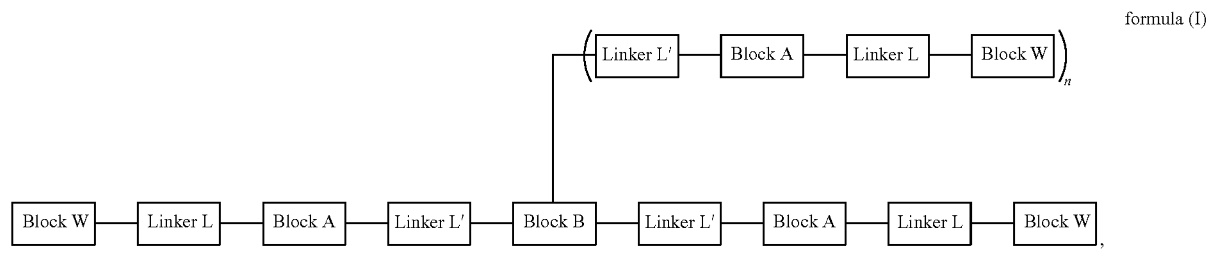

wherein n is an integer from 0 to 4 (e.g., n=1, 2, 3, or 4);

Block B comprises an oligomer derived from a polyester, polalkylene glycol, polysilicone, or polycarbonate with a MW≤4,000 g/mol;

Block A comprises an optionally substituted $C_1$-$C_6$ alkylene, wherein Block A is derived from a diisocyanate crosslinker;

Block W comprises an optionally substituted $C_0$-$C_3$ alkylbenzene-diol or optionally substituted $C_0$-$C_3$ alkylbenzene-triol;

Linker L' comprises a carbamate; and

Linker L comprises a urea.

9. The method of claim 1, wherein the frequency of the ultrasonic energy is 70 KHz.

10. The method of claim 1, wherein from 1.5 to 5.0 J of energy is applied.

11. The method of claim 1, wherein the ultrasonic energy is applied in an amount sufficient to displace fluids between the adhesive composition and the bone fragment prior to the formation of the first anchor and the second anchor.

12. The method of claim 1, wherein the ultrasonic welder comprises a horn tip with individual texture elements, and wherein the individual texture elements are evenly spaced apart with uniform depths of up to 0.127 mm.

13. The method of claim 1, wherein (i) the support structure and (ii) at least one of the first anchor and the second anchor are arranged to form an adhesive portion and a support portion that forms a backing to the adhesive portion, and wherein the adhesive portion when heated is capable of softening without deformation of the support portion.

14. The method of claim 13, wherein the backing portion has a thickness of from 0.05 to 0.31 mm, optionally wherein the backing portion has a thickness of from 0.12 to 0.20 mm.

15. The method of claim 13, wherein the adhesive portion has a thickness of from 0.05 to 0.16 mm, optionally wherein the adhesive portion has a thickness of 0.075±0.025 mm.

16. The method of claim 15, wherein the adhesive portion has a thickness of 0.13±0.03 mm.

17. The method of claim 1, wherein the heating comprises application with a welder via a series of consecutive welding tacks normal to an application surface so as to cover all of the application surface.

18. The method of claim 1, wherein the heating comprises continuous sliding of a welder across an entire device surface in a brushstroke or painting motion.

* * * * *